(12) United States Patent  
Karerangabo et al.

(10) Patent No.: US 9,399,755 B2  
(45) Date of Patent: Jul. 26, 2016

(54) APPARATUS AND METHODS FOR CELL CULTURE

(75) Inventors: Didier Karerangabo, Brussels (BE); Julien Cardon, Seneffe (BE); Jose Antonio Castillo Gonzalez, Brussels (BE)

(73) Assignee: PALL ARTELIS, Brussels (BE)

( * ) Notice: Subject to any disclaimer, the term of this patent is extended or adjusted under 35 U.S.C. 154(b) by 200 days.

(21) Appl. No.: 13/697,491

(22) PCT Filed: May 11, 2011

(86) PCT No.: PCT/EP2011/057621  
§ 371 (c)(1),  
(2), (4) Date: Nov. 12, 2012

(87) PCT Pub. No.: WO2011/141512  
PCT Pub. Date: Nov. 17, 2011

(65) Prior Publication Data  
US 2013/0059339 A1 Mar. 7, 2013

(30) Foreign Application Priority Data

May 11, 2010 (GB) .................................. 1007855.8  
May 11, 2010 (GB) .................................. 1007861.6  
May 11, 2010 (GB) .................................. 1007863.2

(51) Int. Cl.  
*C12M 1/00* (2006.01)  
*C12M 3/00* (2006.01)  
(Continued)

(52) U.S. Cl.  
CPC ............... *C12M 23/22* (2013.01); *C12M 25/06* (2013.01); *C12M 41/46* (2013.01); *Y02P 20/582* (2015.11)

(58) Field of Classification Search  
CPC ...... C12M 23/34; C12M 25/06; C12M 27/18; C12M 27/20; C12M 27/22  
See application file for complete search history.

(56) References Cited

U.S. PATENT DOCUMENTS

| 4,307,193 A | 12/1981 | Iizuka |
| 4,654,308 A | 3/1987 | Safi et al. |
| 4,734,373 A * | 3/1988 | Bartal ........................ 435/299.2 |

(Continued)

FOREIGN PATENT DOCUMENTS

| CN | 101208422 A | 6/2008 |
| CN | 101316925 A | 12/2008 |

(Continued)

OTHER PUBLICATIONS

Corning® CellSTACK® Culture Chambers Grow More Cells with Corning.

*Primary Examiner* — Nathan Bowers  
(74) *Attorney, Agent, or Firm* — King & Schickli, PLLC

(57) ABSTRACT

A bioreactor (1) for the culture of cells (C) comprising a stack of carriers (7) for cell (C) adherence and liquid medium (M) distribution. The carriers (7) are stacked so as to define levels (6) between adjacent carriers (7) for the flow of the liquid medium (M). Adjacent levels (6) are fluidly interconnected via open spaces (2) so that the liquid medium (M) can flow from one level (6) to an adjacent level (6). The open spaces (2) between a first and an adjacent second level (6') do not overlap with the one or more open spaces (2) between the second level (6') and an adjacent third level (6"). One or more of the carriers may also include an area adapted to prevent cell adhesion or growth, thereby allowing for the viewing of cell growth on adjacent carriers from a vantage point external to the bioreactor. Related methods are also disclosed.

29 Claims, 16 Drawing Sheets

(51) Int. Cl.
*C12M 1/12* (2006.01)
*C12M 1/34* (2006.01)

(56) References Cited

U.S. PATENT DOCUMENTS

| | | | |
|---|---|---|---|
| 5,190,878 A * | 3/1993 | Wilhelm | 435/297.2 |
| 5,658,797 A * | 8/1997 | Bader | 435/284.1 |
| 6,368,838 B1 | 4/2002 | Singhvi et al. | |
| 6,562,616 B1 * | 5/2003 | Toner et al. | 435/293.1 |
| 6,824,749 B2 | 11/2004 | Leloup et al. | |
| 7,078,228 B2 | 7/2006 | Lacey et al. | |
| 7,745,209 B2 | 6/2010 | Martin | |
| 2001/0055803 A1 | 12/2001 | Wall | |
| 2002/0182721 A1 | 12/2002 | Nishiguchi et al. | |
| 2007/0218554 A1 | 9/2007 | Miyake et al. | |
| 2009/0298164 A1 | 12/2009 | Cattadoris et al. | |
| 2010/0216229 A1 | 8/2010 | Kenney et al. | |
| 2010/0255576 A1 | 10/2010 | Wilson et al. | |
| 2012/0129257 A1 * | 5/2012 | Yu et al. | 435/395 |

FOREIGN PATENT DOCUMENTS

| | | |
|---|---|---|
| GB | 2338243 A | 12/1999 |
| JP | 52099284 A | 8/1977 |
| WO | 8800235 A1 | 1/1988 |
| WO | 20070039600 A1 | 4/2007 |
| WO | 2009066769 A1 | 5/2009 |
| WO | 2009148512 A2 | 12/2009 |
| WO | 2010014902 A1 | 2/2010 |
| WO | 2010042072 A1 | 4/2010 |

* cited by examiner

APPARATUS AND METHODS FOR CELL CULTURE

FIELD OF THE INVENTION

The disclosure relates to an apparatus for cell culture, to a method of manufacture and operation of the same and to uses of the device for the culture of adherent cells, for the culture of stem cells or primary cells, for the culture of mammalian cells, and for the production of antibodies or viruses, such as for human and/or animal therapies or vaccines.

BACKGROUND OF THE INVENTION

Cell culture of eukaryotic cells that is commercially relevant can be divided into two classes: the cell lines and the primary or stem cells. The cell lines are relevant for the preparation of vaccines (viruses) and of proteins, e.g., antibodies. The cell is used as a bioreactor, the cell is thus nothing else than a host. It can be genetically engineered: one introduces into the cell a gene sequence whose gene product one desires to be produced by the cells. This class of cells can be grown in a fixed bed bioreactor such as disclosed in WO 2007/039600A, the disclosure of which is incorporated herein by reference. When dealing with stem cells, the cells themselves can be harvested and are accordingly the product. The product can be used, for example, for regenerative medicine and for tissue engineering.

Experiments have shown that the culture of certain types of cells such as stem cells is much more delicate than the culture of cell lines, due to several factors. The cells turn out to be very sensitive to mechanical stresses and other external influences. Typical procedures in use in the production of cell lines both to expand and to harvest cells out from a bioreactor are often not appropriate for stem cells; they easily damage or kill all the stem cells.

Currently, stem cells are typically grown in stationary conditions, in tissues culture flasks, put in an incubator. For sake of clarity, "culture flasks" refers to all stationary culture devices, as T-Flasks, Petri dishes, Cell Factories Cell stacks and so on. Roller bottles are also associated with culture flasks. These stationary flasks are provided with a filter for gas exchange. The incubator comprises a plurality of T-flasks, each one constituting a substrate suitable for cell culture upon provision of adequate nutrition. Such systems have the disadvantage of being highly inefficient in terms of the available surface per unit volume. Moreover, the preparation of cell growth takes time: filling T-flasks occurs by inserting a dedicated liquid (e.g., dispersion, suspension or the like) comprising cells to be grown and nutrition, and thereafter turning the T-flask upside down once or more than once to distribute the cells over the available levels. In addition, this operation needs to be repeated several times for each batch/each patient, based on the number of T-flasks requested to produce the sufficient amount of cells needed for a treatment.

Accordingly, a need is identified for an apparatus that addresses the limitations of such devices and others.

SUMMARY OF THE INVENTION

It is therefore an object of the present invention to provide an alternative bioreactor. Advantages of embodiments of the present invention include that they allow more cost effective culture of cells, particularly of stem cells and/or primary cells, while nevertheless allowing cells to be attached to a surface, and/or provide good growth in two dimensions and/or allow harvesting of the cells with a desired quality level.

The object of the present invention is met by embodiments of a first aspect of the present invention. In the first aspect of the present invention, a bioreactor for the culture of cells is provided.

In an embodiment of the first aspect, the disclosure relates to an apparatus for the culture of cells. The apparatus comprises a plurality of carriers for cell adherence and liquid medium distribution. The carriers are stacked to define levels between adjacent carriers for the flow of liquid medium. The levels are fluidly interconnected via one or more open spaces in the carriers so that the liquid medium can flow from one level to an adjacent level. The one or more open spaces between a first and a second level adjacent to the first level do not overlap with each other.

In an embodiment of the first aspect, the disclosure relates to a bioreactor for the culture of cells, comprising a stack of carriers in the form of plates or membranes having surfaces for cell adherence and along which liquid medium can be distributed. The carriers define levels between adjacent surfaces for the flow of liquid medium, wherein the levels are interconnected via one or more open spaces in each of the surfaces so that liquid medium can flow from one level to an adjacent level. The one or more open spaces in a first carrier do not overlap with the one or more open spaces in an adjacent second carrier when projected perpendicularly upon the second carrier. In other words, a first open space in a first and second carrier on opposite side of a single level are mutually laterally or rotationally displaced, when the first open space in the first carrier is seen in a perpendicular projection upon the second open space in the second carrier. The levels defined between adjacent carriers are preferably hermetically closed at the side edges of the carriers. This forces the liquid medium to use the open spaces within a carrier to go from one level to an adjacent level.

The top and/or the bottom carrier of the stack, although not being common to adjacent levels, may nevertheless possess any of the characteristic of any embodiment of the first aspect of the disclosure. For instance, these carriers may possess a plurality of open spaces in so that liquid medium can flow across the top or bottom carrier (to either enter or exit the stack). The adjacent carrier in the case of a bottom carrier is situated above it while the adjacent carrier in the case of the top carrier is situated below it. In the case of any other carrier than the top or the bottom one, an adjacent carrier is the carrier below or above. Preferably, it is the next carrier in the direction of the flow imposed by the driving means (and, most preferably, the carrier above).

In an embodiment, at least one of the carriers may be provided by single solid carrier (e.g., a plate or a membrane) wherein the one or more open spaces are apertures in the solid carrier. The carriers are preferably provided by plates or membranes. The plates or membranes can be non-porous or porous (with pores smaller than 0.05 mm so that the flow through the material is dominated by flow through the open spaces (e.g. circular apertures) rather than through the pores), and preferably comprise rigid plates. Optionally, the carriers may be non-porous at least in the area away from the interconnecting open spaces.

Alternatively, macroporous materials may be used provided the flow through the material is dominated by flow through the apertures rather than through the pores. For example, impermeable textiles can be used. Plastic materials can also be used, such as rigid polystyrene plates.

In an embodiment, at least one of the carriers may be provided by a set of solid carriers (e.g., plates and/or membranes) laterally separated by the one or more open spaces. In the case where a set of solid carriers are laterally separated by one or more open spaces, the solid carriers are either all in the same plane (if the carrier is perpendicular to the principal direction), or are all part of the same conical or pyramidal surface (if the carrier is oriented in a direction non-perpendicular to the principal direction). The open spaces in the carrier serve as fluid interconnects between adjacent levels. In an embodiment, the ratio between the overall surface area covered by the open spaces and the overall area covered by the solid carrier(s) in each carrier may range from 1% to 20%, preferably 1% to 15% and more preferably 1% to 10%. The portion of the carrier area represented by this overall surface area is preferably kept as small as possible so that the surface available for carrying the cells remains as large as possible. However, a flow of liquid medium high enough and homogeneous enough for assuring a good oxygenation and nutrient supply for every cell requires this portion of the carrier area to be large enough. Embodiments of the disclosure may meet both the cell carrier area requirement and the oxygenation/nutrient requirement.

In an embodiment, the open spaces may have an aspect ratio (ratio of the length on the width) from 1 to 4, preferably from 1 to 2.

In an embodiment, the open spaces may be circular.

In an embodiment, independently of the shape of the open spaces, the width of the open spaces may be 0.05 mm or more, 0.1 mm or more, 0.2 mm or more, 0.5 mm or more, 2 mm or less, 1 mm or less, 0.5 mm or less. Measures above 0.05 mm are preferred to allow for the passage of the cells.

In an embodiment, independently of the size and shape of the open spaces, the number of open spaces per unit area of a laminar carrier is preferably such that the ratio between the surface area covered by the ensemble of the open spaces for fluidic interconnection and the surface area of the solid carriers for cell adherence is preferably 20% or less, more preferably 15% or less and most preferably 10% or less. Preferably, it is 1% or more.

In an embodiment, the number of the open spaces per unit area of a laminar carrier may be constant on the whole surface of said laminar carriers. This density of open spaces (holes) may be for instance from 0.001 to 100 open spaces/mm$^2$, from 0.03 to 60 open spaces/mm$^2$ or from 0.1 to 10 open spaces/mm$^2$.

In one embodiment, a plurality of open spaces is present in a first laminar carrier and each of these open spaces are embodied as circular holes through the laminar carrier (e.g. plate or membrane) having a diameter that is less than 1/10th of the diameter of the first laminar carrier, preferably less than 1/50th, more preferably less than 1/100$^{th}$, most preferably less than 1/1000$^{th}$. In this embodiment, the number of open spaces per plate may for instance be from 2 open spaces to $4*10^7$ open spaces, from 10 open spaces to $10^7$ open spaces, from 100 open spaces to $10^6$ open spaces, from 1000 open spaces to $10^5$ open spaces or from 5000 open spaces to 20000 open spaces. The number of open spaces is of course highly dependent on the size of the laminar carrier. In this embodiment, the number of open spaces per laminar carrier is then suitably higher than 25, preferably higher than 50, more preferably at least 100 and most preferably at least 1000. The diameter of the open spaces is preferably from 0.05 mm to 2 mm, more preferably from 0.1 mm to 1 mm, still more preferably from 0.2 mm to 0.5 mm. This allows for the passage of cells.

In another embodiment, the open spaces are groove-shaped. The number of groove-shaped open spaces per carrier is preferably from 1 to 30, more preferably from 2 to 20, more preferably from 4 to 25, still more preferably from 8 to 20 and even more preferably from 12 to 18 (e.g., 16). If a number n of groove-shaped open spaces per carrier are present, two adjacent carriers have their open spaces mutually displaced by a rotation of ½ n turn.

The width of the grooves is preferably from 0.05 mm to 2 mm, more preferably from 0.05 mm to 0.5 mm, even more preferably from 0.05 mm to 0.1 mm to allow for the passage of cells. In the case of grooves widening from the centre to the edge of the laminar carrier, the larger portion of the grooves has preferably a width of from 0.05 mm to 1 mm, more preferably from 0.05 mm to 0.5 mm, even more preferably from 0.05 mm to 0.1 mm In an embodiment, independently of the shape of the open spaces, the smallest dimension of the open spaces may be 0.05 mm, preferably 0.1 mm, more preferably 0.5 mm, most preferably 1 mm.

In an embodiment, the open spaces have a shape and dimensions allowing the passage of a spherical object of 0.05 mm diameter, preferably 0.1 mm diameter, more preferably 0.5 mm diameter, most preferably of 1 mm diameter.

Preferably, such groove shaped open spaces extend over a major portion between the center and an edge of the major surface (e.g., a major portion of a radius in the case of a circular carrier) of a plate or membrane. Referring to FIG. 15 (wherein the carrier comprises a set of solid carriers laterally separated by open spaces), an embodiment is shown wherein groove shaped open spaces extend over the whole portion between a center and an edge of the carrier. Grooves are advantageous as they are more efficient in distributing the liquid medium equally to substantially all points of a carrier. Circular holes, due to their discontinued nature, distribute the flow of liquid less homogeneously. In embodiments, the groove shaped open spaces may be subdivided into a series of groove-shaped trenches, which improves rigidity of the carrier.

For instance, ridges can be present on a carrier, either bridging carriers separated by grooves or part of a same carrier separated by grooves. Such bridging ridges improve the rigidity of the carrier and therefore of the device as a whole. Such bridging ridges are preferably not penetrating the open spaces. Moreover, the architecture of the bioreactor of the disclosure preferably does not frustrate harvesting of the cells. In accordance with an embodiment of the invention, the open spaces are designed so as to be appropriate for flow of medium and cells. In other words, the open spaces are also intended for use during harvesting and not merely for circulation purposes.

In an embodiment, the minimum dimension of the open spaces is 0.05 mm, preferably 0.1 mm, more preferably 0.5 mm and most preferably 1 mm. This permits passage of cells without damaging them.

In an embodiment, at least one of the open spaces becomes wider with increasing radial distance from the geometrical center of the carrier. This is especially advantageous in the case of grooves. This helps equalizing of the flow rate on the whole carrier surface.

In an embodiment, the open spaces in a carrier may be located rotationally symmetrically around the center. This is advantageous as it provides a relatively homogeneous distribution of the medium over the individual levels. Moreover, if the shape of the carriers is circular, stacking of the carriers is simplified as a rotation of a level in the stack never leads to a carrier edge standing out of the stack. This is not the case with other carrier shapes such as oval or rectangular shapes. Such other shapes are however not excluded.

In embodiments, the surface area of the carrier (including the surface covered by the open spaces in the carrier) may be from 50 cm$^2$ to 1 m$^2$, preferably from 75 cm$^2$ to 0.8 m$^2$.

For instance, in embodiments wherein the carriers are circular, their diameter may be from 10 to 100 cm.

The thickness of the carrier is preferably as thin as possible for allowing a higher number of carriers in a volume as small as possible. For instance, carriers having a thickness of from 0.4 to 2 mm or from 0.6 to 1 mm can be used.

In an embodiment, the overall surface area covered by the open spaces in at least one of carrier increases faster with increasing radial distance to the geometrical center of the carrier. This is advantageous because it reduces the difference in flow rate experienced by the cells close to the geometrical center of the carrier and by the cells farther away from the geometrical center of the carrier. This allows optimization so that the flow rate can be made substantially equal at every distance of the geometrical center of the carrier. Preferably, the open spaces have a surface area and are designed and/or distributed such that the overall surface area of open spaces increases with increasing radial distance to a center. This turns out to improve homogeneity of the flow rate across the bioreactor. It is observed for clarity that this increased overall surface area may be obtained by increase of the width of single open spaces. Alternatively or additionally, it may be obtained by increase of the number of open spaces. The increase in surface area may be continuous or could be discontinuous, e.g., stepwise. In case that the bioreactor has a cylindrical shape, which is preferred, the increase of overall surface area will be independent of the location or phase of the open spaces. In case that the bioreactor has another shape, for instance with an oval or rectangular cross-section perpendicular to the principal direction, the increase in surface area may be different for different directions away from the center.

In an embodiment, the overall surface area covered by the open spaces in at least one of the plates or membranes increases faster with increasing radial distance to the geometrical center of the carrier in such a way that the flow rate is substantially equal at every distance of the geometrical center of the carrier.

In all embodiments, the one or more open spaces in a first carrier do not overlap with the one or more open spaces in an adjacent second carrier when projected perpendicularly upon the second carrier. This is advantageous because this prevents the liquid medium from travelling in a straight line between adjacent levels and forces at least some of the liquid medium to flow laterally within a level before being able to reach an adjacent level (typically the adjacent upper level). Although the global flow of the liquid medium is along the principal direction (e.g., the liquid may globally travel from the bottom of the stack of carriers up to the top of the stack), the liquid medium spends more time flowing (e.g., laterally) within a level than across (e.g., vertically) adjacent levels. This enables the liquid medium to reach all area of each surface of a carrier and permits therefore to have substantially the same flow everywhere in the bioreactor.

In other words, first open spaces in a first and second carrier on opposite side of a single level are mutually rotationally or laterally displaced, when the first open space in the first carrier is seen in a perpendicular projection upon the second carrier. With such a rotational or lateral displacement, a risk is avoided that a set of open spaces defines a columnar channel extending over several levels. In an implementation thereof, the at least one open space in the first carrier is provided with a first phase between a lower and an upper angle, the phase being defined as a phase or orientation around a center of the level. The open space in the second carrier is provided with a second phase between a lower and an upper angle, wherein the first phase does not overlap with the second phase.

An embodiment of the first aspect relates to a bioreactor for the culture of cells, comprising a stack of laminar carriers for cell adherence and liquid medium distribution, said laminar carriers being stacked in a principal direction, each pair of adjacent laminar carriers within said stack being separated from one another by an average distance so as to define a level between said adjacent laminar carriers for the flow of said liquid medium, wherein adjacent levels are fluidly interconnected via a plurality of open spaces in a laminar carrier common to said adjacent levels so that said liquid medium can flow between said adjacent levels, wherein said open spaces in a laminar carrier have a width at least five times and preferably at least ten times smaller than the average distance separating said laminar carrier from an adjacent laminar carrier, and wherein said width is at least 0.05 mm. It has been surprisingly observed that when the open spaces have a width at least five times and preferably at least ten times smaller than said average distance, even in the case when the open spaces of a first laminar carrier overlap when projected perpendicularly upon the open spaces of a second laminar carrier, the liquid medium do not travel in a straight line between adjacent levels and at least some of the liquid medium flow laterally within a level before being able to reach an adjacent level (typically the adjacent upper level). Although the global flow of the liquid medium is along the principal direction (e.g. the liquid may globally travel from the bottom of the stack of laminar carriers up to the top of the stack of laminar carriers), the liquid medium spends more time flowing (e.g. laterally) within a level than across (e.g. vertically) adjacent levels. This enables the liquid medium to reach all area of each surface of a laminar carrier and permits therefore to have substantially the same flow everywhere in the bioreactor.

In an embodiment wherein said open spaces in a laminar carrier have a width at least five times and preferably at least ten times smaller than the average distance separating said laminar carrier from an adjacent laminar carrier, and wherein said width is at least 0.05 mm, the open spaces may have an aspect ratio (ratio of the length to width) from 1 to 4, preferably from 1 to 2.

In an embodiment wherein said open spaces in a laminar carrier have a width at least five times and preferably at least ten times smaller than the average distance separating said laminar carrier from an adjacent laminar carrier, and wherein said width is at least 0.05 mm, the open spaces may be circular.

In an embodiment, wherein said open spaces in a laminar carrier have a width at least five times and preferably at least ten times smaller than the average distance separating said laminar carrier from an adjacent laminar carrier, and wherein said width is at least 0.05 mm, independently of the shape of the open spaces, the width of the open spaces may be 0.05 mm or more, 0.1 mm or more, 0.2 mm or more, 0.5 mm or more, 2 mm or less, 1 mm or less, 0.5 mm or less. Measures above 0.05 mm are preferred to allow for the passage of the cells.

In an embodiment wherein said open spaces in a laminar carrier have a width at least five times and preferably at least ten times smaller than the average distance separating said laminar carrier from an adjacent laminar carrier, and wherein said width is at least 0.05 mm.

It must be noted that the top and/or the bottom laminar carrier of the stack, although not being common to adjacent levels, may nevertheless possess any of the characteristic of any embodiment of the first aspect of the present invention. For instance they may possess a plurality of open spaces in so that said liquid medium can flow across said top or bottom laminar carrier (to either enter or exit the stack of layer), wherein said open spaces in a laminar carrier have a width at least five times and preferably at least ten times smaller than the average distance separating said laminar carrier from an adjacent laminar carrier, and wherein said width is at least 0.05 mm. The adjacent laminar carrier in the case of a bottom laminar carrier is situated above it while the adjacent laminar carrier in the case of the top laminar carrier is situated below it. In the case of any other laminar carrier than the top or the bottom one, an adjacent laminar carrier is the laminar carrier below or above. Preferably, it is the next laminar carrier in the direction of the flow imposed by the driving means. Preferably, it is the laminar carrier above.

Within the stack of carriers, the laminar carriers are preferably parallel to each other. In this case, the average distance is a fixed distance.

The average or fixed distance between two laminar carriers is preferably from 0.5 to 10 mm, preferably from 1 to 5 mm, more preferably from 1 to 3 mm and even more preferably from 1.2 to 2 mm. The present embodiment has the advantage of viably (for the cells) enabling such a small inter-level distance. In static cell culture devices, such a small inter-level distance would not permit enough space above the cells to permit sufficient oxygenation of the cells. Also, the presence of a plurality of open spaces in the laminar carriers, wherein said open spaces have a width at least five times and preferably at least ten times smaller than said average distance enable such small inter-level distances to be used by decreasing the time necessary for the liquid medium to travel from the bottom to the top of the stack of laminar carriers while simultaneously decreasing the liquid flow experienced by the cells.

In a further embodiment, the minimum dimension of the open spaces is at least a tenth and preferably at least a fifth of the distance between two carriers.

In a further embodiment wherein said open spaces in a laminar carrier have a width at least five times and preferably at least ten times smaller than the average distance separating said laminar carrier from an adjacent laminar carrier, and wherein said width is at least 0.05 mm, the minimum dimension of the open spaces is at least a tenth and preferably at least a fifth of the distance between two laminar carriers.

In a further embodiment, at least some of the carriers have at least one side edge provided with at least one ridge, ridges of first and second adjacent carriers defining a mutual distance between the carriers at the side edge. This arrangement provides structural stability. The ridge may extend on a first (e.g., top) side and/or on a second (e.g., bottom) side of the side edge. The ridges may be continuous along the side edge. Alternatively, the ridges may be block-shaped and mutually separated by spaces. Block-shaped ridges of an adjacent carrier may extend into such spaces. This allows the definition of a mutually fixed position. In other words, female and male notches for plate positioning may be present at the edge of each carrier. Ridges may also project outward from the edges.

In an embodiment, the levels defined between adjacent carriers are closed at the side edges of the carriers. The closure of the side edges of the carriers will result in defining the side outer surface of the bioreactor. The stacking occurs in one embodiment by means of mechanical connections defining the side wall of the columnar channel. These mechanical connections may fix the orientation of each carrier in the stack, but alternatively may leave freedom for independent rotation of each of the carriers. Clearly, it is by no means excluded that the stack of carriers including the columnar channel is manufactured as one piece, for instance by means of a moulding process, and/or that adhesive or mechanical fixtures (screw or the like) are used for fixing portion of the stack. However, separate manufacture of the carriers has the advantage that the stack becomes modular, so as to be made larger or shorter dependent upon the intended use and needed conditions.

Preferably use is made of the ridges for providing a closure. The closures of the levels may be obtained by connecting ridges (e.g., ridges projecting outward from the edges) with a polymer material. Such polymer materials include adhesives, resins and the like. The polymer material may be applied as a liquid or sheet like material and then be processed, for instance dried, cross-linked or may be first melted and then allowed to cool down and solidify. The polymer material may alternatively be moulded into a desired shape, for instance by insert-moulding or transfer moulding.

The stack of carriers may comprise from 5 to 500 carriers defining from 5 to 500 levels. Since two adjacent carriers define one level, the number of levels is normally the number of carriers minus one. However, the top carrier of the stack is usually also usable for the culture of cells which means that the number of carriers can be equal to the number of levels.

The number of levels and/or carriers within one bioreactor is for instance in the range of 5 to 500, preferably in the range of 80 to 200 and more preferably in the range of 130 to 180.

Preferably, all carriers are structurally the same, i.e., have the same dimensions, the same orientation, the same area ratio open spaces/carrier and have open spaces having the same shapes and dimensions. This allows for the same flow rate at each level. Preferably, the average or fixed distance is the same for each pair of laminar carrier in the stack of laminar carrier. This also permits to have the same flow rate at each level. Such equal flow rate (within a level and/or between level) may be desired, even if not essential, in order to guarantee that same culture conditions apply everywhere inside the bioreactor.

With the relatively constant distribution across each carrier and primarily lateral flow direction, the cells may be attached to the carrier and a good cell growth based on a two-dimensional culture may be obtained. The open spaces in a carrier may be suitably embodied as apertures in the form of holes or grooves.

In a preferred embodiment of the disclosure, each carrier of the stack comprises at least two open spaces. In such a case, the bioreactor of the disclosure can be considered to be composed of a plurality of fluid interconnects that are coupled both in series and in parallel. This combination of series and parallel coupling of fluid interconnects—which are effectively portions of a level—turns out better than either a series coupling or a parallel coupling of fluid interconnects alone. If the fluid interconnects were coupled merely in series, they would extend merely laterally on one level. In particular, the medium would flow on a first level from a first aperture to a distant second aperture and then back on a subsequent second level and so on. When each carrier of the stack comprises at least two open spaces, the flow rate can be lower than if only one open space per carrier is present while keeping the same circulation time. The shear stress can therefore be made lower or the circulation time can be reduced. In the case of only one open space per carrier the circulation time can be very high, e.g., easily a couple of hours, with a flow rate that limits shear stress (for instance equal to or smaller than 2 mm/s).

Useful embodiments when only one open space is present per plate are for instance embodiments where an external circulation system is used and wherein alternating carriers in the stack have alternatively a central open space and a peripheral open space. The carriers in this embodiment are of two alternative kinds. For instance, a first kind is hold in place by its edge attached to an external wall and has a central open space. In this example, a second kind is hold in place by being attached to a central axis and assures an open space for fluidly interconnecting two adjacent levels by not extending to the wall closing the stack. Of course, the central axis can be a fluid channel (e.g., a hollow tube) concentric and internal to the stack of carriers. This hollow tube forms a fluid channel separate from the stack of carriers providing a fluid connection between a first carrier at a first extremity of the stack of carriers and a second carrier at a second extremity of the stack of carriers, therewith providing a circulation system for the liquid medium.

Alternatively, if the fluid interconnects were merely coupled in parallel, one fluid interconnects would likely be shorter than another one. Hence pressure drop would be inhomogeneous within the bioreactor, leading to differences in flow rate within the system. Such major differences in flow rate are undesired, as they may lead to turbulence and/or inhomogeneities that may easily damage cells and cell growth. Moreover, flow rate in some fluid interconnects of the bioreactor may be low. This will typically lead to dead zones (zones with poor mixing) and, consequently, differences in cell growth over the bioreactor. In a worst case scenario, cell culture in certain fluid interconnects would not lead to an adequate final product of the desired quality.

Moreover, the serial and parallel coupling of fluid interconnects prevents that a single obstruction of a fluid interconnects (e.g., an open space or aperture) blocks substantially all further flow.

In an embodiment, the reactor is provided with a first and an opposite second side (e.g., a bottom and a top) and comprises a stack of carriers as defined in any embodiment of the first aspect of the disclosure, e.g., that are stacked in a principal direction from the first side (e.g., the bottom of the reactor) to the second side (e.g., the top of the reactor), so as to define levels between adjacent carriers for the culture of the cells and flow of medium. It will be understood by the skilled person that the bioreactor is at its second side (e.g., top) preferably closed so as to maintain physical conditions in the best manner. In embodiments, the top and/or bottom of the reactor may comprise inlet and/or outlet (e.g., an inlet and outlet for gas) and/or probes (e.g., a temperature probe, pH probe, dissolved $O_2$ probe, dissolved $CO_2$ probe, biomass probe or any other probe). The top and/or bottom may also be at least partly transparent to allow microscope mediated observation. For instance, the first and/or second side may comprise optically transparent windows.

In an embodiment, the reactor may comprise at least one probe for measuring a parameter of the liquid medium (e.g., a physical, chemical or biological parameter such as the temperature, the pH, the $O_2$ concentration, the $CO_2$ concentration, the cell density in the medium (biomass), among others).

The bioreactor may further comprise a controller connected to the probe for modifying the parameter in function of the input received by the controller from the probe. In embodiments, the bioreactor may further comprise means for modifying the parameter. In embodiments, the means are connected to the controller. Examples of such means are heating means, cooling means, gas delivery means and driving means amongst others.

In another embodiment, the bioreactor further is provided with a pump or medium circulation means (e.g., an impeller) for circulation of the medium in the principal direction. The advantages are among others better aeration, heat transfer and possibility of control. Furthermore, in accordance with the disclosure, fluid circulation is enabled such that medium can be circulated also during harvesting.

In this manner, the bioreactor of the invention provides a two-dimensional structure for cell culture with appropriate medium flow and harvesting.

The risk of generating an entirely vertical flow of the medium over several levels that leads to an inhomogeneous distribution of cells and medium, which can be reduced by having the width of the open spaces at least five times smaller than the distance between two laminar carriers or which can be reduced by having open spaces not overlapping between adjacent laminar carriers, may be is alternatively or additionally reduced by means of the shape of the fluid interconnects and/or through active flow stimulation. The latter active flow stimulation is suitably arranged through a circulation means (e.g., an impeller such as a mechanical impeller and preferably a magnetic impeller) as known in the art. The impeller is suitably provided in an upper cavity above the stack of laminar carriers and adjacent to it or in a lower cavity at a bottom of the bioreactor (under the stack of laminar carriers) and adjacent to it. Alternatively, a first impeller is present in the lower cavity and a second impeller is present in the upper cavity, so as to allow operating the bioreactor upside down. Preferably, bearings are provided in the lower and/or upper cavity for positioning said impeller. The impeller can be present in the fluid channel (e.g., in a central and concentric column providing a fluid connection between said first laminar carrier and said second laminar carrier and providing a circulation system for the liquid medium) This is especially advantageous when no lower cavity is present.

In an embodiment of the disclosure, the bioreactor may further comprise a top zone and a bottom zone adjacent to respectively the first and the second extremity of the stack of carriers and in fluid communication therewith and with the central fluid channel.

In an embodiment of the disclosure, the bioreactor may further comprise inlet/outlet ports to the top and/or bottom zone.

In an embodiment of the disclosure, at least one inlet port may be present in the bottom zone and at least one outlet port may be present in the top zone and external circulation means such as a pump may be coupled between the inlet and outlet ports.

In again another embodiment, at least some of the carriers have a portion that is oriented in a direction including a non-perpendicular angle to the principal direction, which portion comprises at least one open space. A preferred implementation hereof is that the carriers have a curved shape, when seen in a cross-sectional side view through a center axis. For instance, the carrier may be conical. Alternatively, the carrier can also be pyramidal. Though it is deemed suitable that substantially all carriers have the same or a similar shape and orientation, this is not deemed necessary. For instance, a first carrier may be of curved (e.g., conical or pyramidal) shape with an edge that is nearer to the first side of the bioreactor than its center, while a second carrier is of curved shape and is provided with an edge that is nearer to the second side of the bioreactor that its center—in other words, the orientation may be opposite. It may further be that the first carrier is flat and the second is of a different shape (e.g., conical). It may further be that the first and the second carriers are curved and have same orientation, but that the curvature of the first carrier differs from that of the second carrier. Such embodiments lead thereto, that a level has varying height, which may be advantageous for improved harvesting. Additionally, a stack may be subdivided into a first and a second substack, between which an inlet and/or outlet for fluid and/or medium may be present. Such port is then suitably coupled to a level with a varying height.

In one further embodiment, physical conditions in the bioreactor may be monitored and controlled adequately. This is deemed beneficial as stem cells/primary cells are very fragile. Slight variations in physical conditions such as temperature, biomass, pH, $O_2$ and $CO_2$-concentrations and mechanical shocks may damage the stem cells. The bioreactor of the disclosure is thereto suitably provided with an upper cavity on top of the stack of carriers and adjacent to the stack of carriers. Sensors may be present at least in the upper cavity.

Sensors may be present inside the bioreactor. In addition or alternatively, composition and physical conditions of the external circulation system, if any, may be monitored, for instance between the outlet port of the bioreactor and the medium storage tank. A separate sensing vessel may be foreseen for this. Typical conditions to be measured include the pH, the temperature, the biomass, the oxygen and $CO_2$ content of the medium, the amount of biological material, and/or the effective flow rate. The bioreactor according to the disclosure may preferably comprise at least one fluid channel separate from the stack of carriers providing a fluid connection substantially extending from the first side to the second side, therewith providing an internal circulation system of medium. An internal circulation system for medium leads to smaller footprint than an external circulation system. Moreover, the number of external components is less than with an external circulation system, which is beneficial for user friendliness. Expressed in other words, in an embodiment, the bioreactor may further comprise at least one fluid channel separate from the stack of carriers providing a fluid connection between a first carrier at a first extremity of the stack of carriers and a second carrier at a second extremity of the stack of carriers, therewith providing a circulation system for the liquid medium. Preferably, the fluid channel is embodied as a columnar channel that is located on a center axis of the bioreactor. In an embodiment, the fluid channel may be concentric to the stack of carriers and internal or external to the stack of carriers. For instance, the fluid channel may be a central column internal to the stack of carriers.

The columnar channel suitably extends between a lower and an upper cavity. An impeller may be present in the lower cavity and/or in the upper cavity. The impeller has preferably its rotational axis confounded with the center axis. As mentioned above, the impeller can be in the columnar channel e.g., if no lower cavity is present. In this case, at least some ports need to be present to interconnect the columnar channel with at least one level (preferably comprising the lowest level of the stack). It is observed that the lower cavity may be separated from the columnar channel by means of a wall having one or more apertures, i.e., access ports for the medium. Such separation allows that the flow in the columnar channel is more vigorous than in the levels of the reactor. In such a manner both an appropriate mixing and an appropriate flow rate for the cells may be achieved. Ports between such columnar channel and individual levels of the bioreactor may be present but are preferably not present. However, as mentioned above, if no bottom cavity is present and if the circulation means or pump is an impeller in the columnar channel, port(s) are preferably present. Suitably, the columnar channel is not provided with such ports, but with means, such as a tube or the like, for providing components into medium within the columnar channel. Examples of such components are gaseous components such as air, oxygen and $CO_2$, but also acid or base to correct pH, or culture medium, or other nutrients or additives. The means may be embodied as a tube, but could alternatively be embodied as means for addition of components in solid form. If the means are embodied as a tube for gas regulation and/or exchange and/or control and regulation of gas (such as oxygen or carbon dioxide concentration), the means could be a simple tube for infecting gas bubbles or could be a closed porous silicon tubing (this avoids bubbles and foam). The columnar channel may then have quite some stirring or at least rotational movement. As a result of which the components, such as oxygen, may dissolve into the medium, and an appropriate mixing is achieved prior to provision of the medium to the levels where cells are growing. Furthermore, any bubbles may leave the medium prior to its provision to the individual levels. Bubbles going through the levels might damage cells and are thus undesired.

Such means for providing components into the medium can also be provided at other locations (e.g., in the upper cavity). A filter for gas exchange can also be provided.

In again a further embodiment, the level comprises a structured fixed bed with cavity sizes adapted to the size of the cells to be expanded.

Moreover, harvesting may be carried out without shaking the bioreactor. Such shaking has the disadvantage of likely destroying grown cells, in case of culture of stem cells or primary cells.

In an embodiment, the carriers of the bioreactor are hydrophilic. This can be achieved via a surface treatment. Surface treatment is advantageous for cell cultivation. Basically, hydrophilisation is suitably carried out by a physical (e.g., vacuum or atmospheric plasma treatment) or a chemical treatment (functionalisation with hydrophilic silanes). Other treatments, more sophisticated, can be envisaged (physical, chemical functionalization for example).

Harvesting may be carried out, such as by an enzymatic reaction (e.g., as with trypsine). Anchoring points on the surface of the carrier may be present for adhesion, though a smooth surface is typically preferred.

In an embodiment, the bioreactor of the disclosure is adapted so that the linear velocity of the medium in the levels is lower than 2 mm/s (e.g., 1 mm/s) and/or so that the circulation time of the medium is lower than 60 minutes (e.g., 30 min). This can be achieved by selecting appropriate level width, open space density, impeller or pumping speed and open space shape and location.

Preferably, the bioreactor is further adapted to permit the linear velocity of the medium to be increased to the range 10 mm/s-20 mm/s for the harvesting step. This helps in detaching the cells from the carriers.

The bioreactor according to embodiments of the disclosure is most suitably used for the culture of animal cells (e.g., mammalian cells, insect cells, fish cells, plant cells or the like), preferably mammalian cells including or not including human cells but preferably including human cells. The bioreactor according to embodiments of the disclosure can be used for the culture of primary cells and/or stem cells. However, it is not excluded that the bioreactor according to the invention finds application for culture of any other type of cell or even any other type of biological material, such as viruses, bacteria and the like.

In a second aspect, the disclosure relates to a method of cultivating cells. In an embodiment of this second aspect, the method comprises the steps of:

Sensing a value of a parameter of the liquid medium (e.g., pH, temperature, $O_2$ concentration, $CO_2$ concentration, . . . ), and Circulating the liquid medium in the bioreactor by operating a circulation means or pump as long as the value of the parameter is below or above a predetermined value.

In a particular embodiment of this second aspect, the method comprises the steps of:

Sensing a value of a parameter of the liquid medium (e.g., $O_2$ concentration), and Circulating the liquid medium in the bioreactor by operating a circulation means or pump as long as the value of the parameter is below a predetermined value.

In another embodiment of this second aspect, the method comprises the following collecting steps once the cells are grown in a bioreactor according to any embodiment of the first aspect of the disclosure:

Emptying the bioreactor from its liquid (culture) medium by opening an outlet for the liquid medium, Introducing another liquid medium comprising a releasing agent (e.g., trypsin), Circulating the other liquid medium within the bioreactor by operating circulation means or pump, Emptying and thereby collecting the grown cells.

In another embodiment of the second aspect of the disclosure, the method comprises the steps of:

Introducing a first liquid medium comprising cells in a bioreactor according to any embodiments of the first aspect of the disclosure, Operating circulation means or pump in order to circulate the first liquid medium in the bioreactor, Stopping the circulation means or pump in order to allow the cells to settle on a first side of the carriers of the bioreactor, and Optionally removing the liquid medium from the bioreactor, introducing a second liquid medium comprising cells in the bioreactor, operating the circulation means or pump in order to circulate the first liquid medium in the bioreactor, stopping the circulation means or pump, turning the bioreactor upside down and allowing the cells to settle on a second side of the carriers of the bioreactor, In a further embodiment of the second aspect of the disclosure, the method comprises a combination of the steps above. For instance, the method may comprise the steps of:

Introducing a first liquid medium comprising cells in a bioreactor according to any embodiments of the first aspect of the disclosure, Operating circulation means or pump in order to circulate the first liquid medium in the bioreactor, Stopping the circulation means or pump in order to allow the cells to settle on a first side of the carriers of the bioreactor, Optionally removing the liquid medium from the bioreactor, introducing a second liquid medium comprising cells in the bioreactor, operating the circulation means or pump in order to circulate the first liquid medium in the bioreactor, stopping the circulation means or pump, turning the bioreactor upside down and allowing the cells to settle on a second side of the carriers of the bioreactor, Sensing the value of a parameter of the liquid medium (e.g., oxygen concentration), Circulating the liquid medium in the bioreactor by operating the circulation means or pump as long as the value of the parameter is below a predetermined value, Once the cells are grown, emptying the bioreactor from its liquid (culture) medium by opening an outlet for the liquid medium, Introducing another liquid medium comprising a releasing agent (e.g., trypsin), Circulating the other liquid medium within the bioreactor by operating a circulation means or pump, Emptying and thereby collecting the grown cells.

Yet another aspect of the disclosure relates to apparatus and methods for monitoring cell growth including multiple stacked carriers. A first carrier positioned above a second carrier may include an area or portion that is adapted to prevent the growth of cells. When this area or portion is aligned with a growth area of an underlying carrier, it allows a line of sight to be maintained from external to the bioreactor and through the first carrier to the growth area.

Still a further aspect of the disclosure relates to a carrier for culturing cells in a bioreactor. The carrier includes a surface having an area adapted for cell adherence and an area adapted for preventing cell adherence. Preferably, the surface for preventing cell adherence is associated with a piece of transparent material, or may be hydrophobic.

A bioreactor for the culture of cells may include first and second carriers, each having at least one inlet for admitting a fluid medium. The first carrier including a first portion adapted for cell adherence, and a second of the carriers further includes a second portion adapted to prevent cell adherence. The second portion of the second carrier thus allows for viewing the first portion of the first carrier when the first and second portions align.

Preferably, the first and second portions comprise surfaces on the carriers, but may form openings as well. The second portion may include an optically transparent material between the second carrier and the first carrier. A single housing may be provided for receiving the carriers, or the carriers may comprise stackable trays or cubes.

A third carrier may be provided having the first portion adapted for cell adherence and a third portion adapted for preventing cell adherence for aligning in use with the second portion of the second carrier.

Still another aspect of the disclosure is a bioreactor for the culture of cells. The bioreactor comprises a stack of carriers. A first of the carriers positioned above a second of the carriers includes an area adapted to prevent cell adherence. The area of the first carrier without cell adherence allows for viewing a cell growth area on the second carrier through the first carrier.

A bioreactor for the culture of cells comprises a stack of N carriers. Carrier N–1 has at least one area adapted to prevent cell adherence. This area of carrier N–1 allows for viewing a cell growth area on carrier N through carrier N–1. Preferably, carrier N–2 has at least two areas adapted to prevent cell adherence, a first of the prevent areas allowing for viewing of a first cell growth area on carrier N–1 and a second of the prevent areas allowing for the viewing of a second cell growth area on carrier N using a line of sight through the prevent area of carrier N–1.

Viewed another way, a bioreactor for the culture of cells comprises a stack of N carriers. Carrier N–M has at least M area(s) adapted to prevent cell adherence. These area(s) of carrier N–M allows for viewing a cell growth area on carrier N through carrier N–M.

The disclosure also related to a bioreactor comprising a stack of N carriers and having an optically transparent line of sight from an external vantage point to a cell growth area on a surface of carrier N–1. Preferably, a column of transparent material forms the optically transparent line of sight.

Viewed another way, a bioreactor comprising a stack of carriers includes an optically transparent solid material positioned in a space between adjacent carriers.

Still a further aspect of the disclosure is a bioreactor comprising a vertical stack of carriers, each having an inlet for receiving a fluid medium, and adapted to allow for viewing a growth area on one carrier through an adjacent carrier other than via the inlet.

Yet another aspect is a bioreactor for the culture of cells comprising a stack of carriers. The carriers are stacked so as to define levels between adjacent carriers for the flow of a liquid medium from an inlet to an outlet of the bioreactor. Adjacent levels are fluidly interconnected via two or more open spaces so that the liquid medium can flow from one level to an adjacent level. At least one of the open spaces provided by a first carrier at least partially overlaps with an open space provided by a second, adjacent carrier to create a substantially unobstructed optical path to view a growth area on a third carrier. Preferably, the carriers further include one or more open spaces between a first and an adjacent second level that do not overlap with the one or more open spaces between the second level and an adjacent third level when projected along the principal direction.

The disclosure also pertains to a bioreactor for the culture of cells comprising a stack of at least three carriers. A first carrier provides at least three open spaces without cell adherence, and at least one open space on the first carrier aligns with at least one open space on a second carrier to allow for viewing a cell growth area on a third carrier. Preferably, the second carrier comprises at least two open spaces.

BRIEF DESCRIPTION OF THE FIGURES

The bioreactor according to the invention will be further elucidated with reference to the figures, in which.

DETAILED DESCRIPTION OF ILLUSTRATIVE EMBODIMENTS

Figure 1:
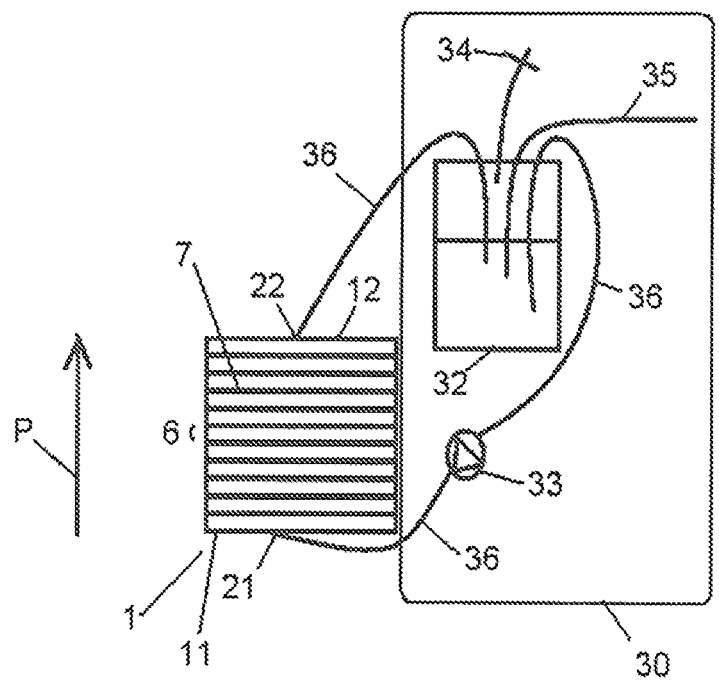
FIG. 1 shows a diagrammatical view of a bioreactor provided with an external circulation system, according to an embodiment of the disclosure.

The disclosure will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention. It should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

Furthermore, some of the embodiments are described herein as a method or combination of elements of a method that can be implemented by a processor of a computer system or by other means of carrying out the function. Thus, a processor with the necessary instructions for carrying out such a method or element of a method forms a means for carrying out the method or element of a method. Furthermore, an element described herein of an apparatus embodiment is an example of a means for carrying out the function performed by the element for the purpose of carrying out the invention.

In the description provided herein, numerous specific details are set forth. However, it is understood that embodiments of the invention may be practiced without these specific details. In other instances, well-known methods, structures and techniques have not been shown in detail in order not to obscure an understanding of this description.

FIG. 1 shows a diagrammatical view of a first embodiment of the bioreactor according to the invention. The bioreactor 1 is provided with a first side 11 and an opposite second side 12. A stack of carriers 7, which are preferably, is present in the bioreactor 1. The carriers are stacked along a principal direction P extending from the first side 11 to the second side 12. The carriers 7 are provided with open spaces (not shown). The bioreactor 1 of this embodiment is provided with an external circulation system 30. The external circulation system 30 comprises a medium storage tank 32 that is coupled to the bioreactor 1 through tubes 36. An external pump 33 is present for enabling flow of medium through the bioreactor 1. Medium flowing through the tubes enters the bioreactor 1 at inlet port 21 on the first side 11 of the bioreactor 1. It passes each carrier 7 within the bioreactor 1 through the open spaces therein, and then leaves the bioreactor at outlet port 22 on the second side 12 of the bioreactor 1. The medium storage tank 32 is in this example provided with a filter 34 for gas exchange and with means or transporter 35 for addition of components. The means 35 may be embodied as a tube, but could alternatively be embodied as means for addition of components in solid form. While the medium storage tank 32 is shown here in a typical laboratory implementation, e.g., a beaker glass, it will be clear that implementations of larger scale are not excluded. While the medium storage tank 32 is shown here to be coupled to a single bioreactor 1, it is not excluded that it is coupled to a plurality of bioreactors 1, suitably arranged in parallel. Though not shown, it is preferred that the composition and physical conditions of the bioreactor 1 are monitored. Hereto, sensors may be present inside the bioreactor. Alternatively, composition and physical conditions of the external circulation system may be monitored, for instance between the outlet port 22 of the bioreactor 1 and the medium storage tank 32. A separate sensing vessel may be foreseen for this. Typical conditions to be measured include the pH, the temperature, the oxygen and $CO_2$ content of the medium, the amount of biological material, and/or the effective flow rate.

Figure 2:
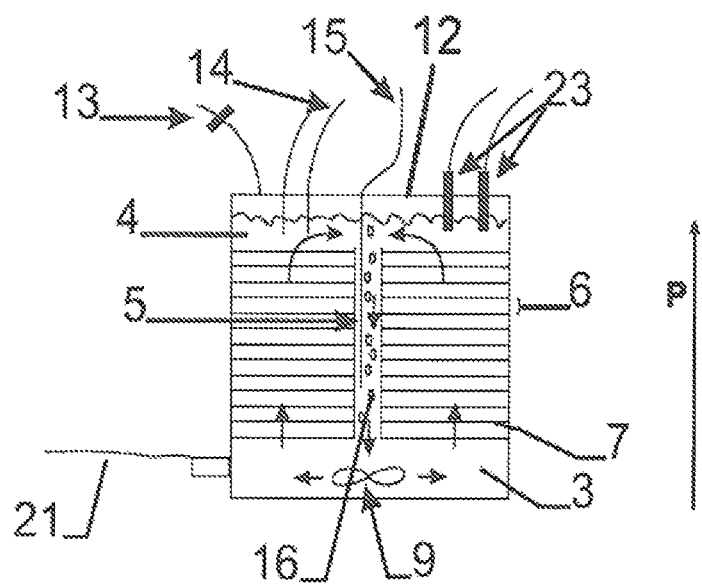
FIG. 2 shows a diagrammatical cross-sectional view of a bioreactor comprising a circulation system integrated in the bioreactor according to an embodiment of the disclosure.

FIG. 2 is a cross-sectional diagrammatical view of a second embodiment of the bioreactor 1. The embodiment shown here is a bioreactor in which a circulation system is integrated. In this example the reactor is provided with a lower cavity 3, an upper cavity 4 and a fluid channel 5 extending between the lower and upper cavity 3, 4 along the principal direction P of the bioreactor 1. The fluid channel 5 is in the example shown here a columnar channel located in the center of the bioreactor 1, which is preferably of cylindrical shape. The carriers 7 are stacked along the same direction. The stacking occurs in one embodiment by means of mechanical connections defining the side wall of the columnar channel 5. These mechanical connections may fix the orientation of each carrier in the stack, but alternatively may leave freedom for independent rotation of each of the carriers. Clearly, it is by no means excluded that the stack of carriers including the columnar channel could be manufactured as one piece, for instance by means of a moulding process, and/or that adhesive or mechanical fixtures (screw or the like) are used for fixing portion of the stack.

However, separate manufacture of the carriers has the advantage that the stack becomes modular, so as to be made larger or shorter dependent upon the intended use and needed conditions.

Preferably, as shown in this FIG. 2, the columnar channel 5 does not have connections to individual levels 6 extending between adjacent carriers 7 in the bioreactor 1. This has the advantage that the columnar channel 5 may be used as a mixing and dissolution vessel. In this example, the bioreactor 1 is provided with several ports 13, 14, 15, e.g., a filter 13 for gas exchange, a port 14 for the addition of liquid components, in particularly a solvent, solution, suspension, dispersion, and a port 15 for the addition of gaseous components, for instance air, oxygen or $CO_2$. Particularly any bubbles 16 resulting from the addition of gaseous components are better prevented from entering the levels 6 between the carriers 7. The bioreactor 1 is provided with an impeller 9 for stirring the medium. The impeller is typically, and particularly in laboratory versions of the present bioreactor 1, a magnetic impeller. However, a mechanically driven impeller is not excluded.

This impeller 9 is further responsible for providing the flow of medium through the bioreactor. However, if desired, a separate pump may be used to control and drive such flow. The impeller 9 may be provided in the lower cavity 3, at the end of the columnar channel 5. It is observed that the lower cavity 3 may be separated from the columnar channel by means of a wall having one or more apertures, i.e., access ports for the medium. Such separation allows that the flow in the columnar channel 5 is more vigorous than in the levels 6 of the reactor 1. In such a manner both an appropriate mixing and an appropriate flow rate for the cells may be achieved.

The bioreactor 1 of this embodiment is provided with at least one inlet port 21 at its first side. This inlet port 21 is primarily intended for filling and emptying of the reactor. However, it is by no means excluded that this inlet port 21 forms the port to an external circulation system that is used in addition to the internal circulation system. In such case, typically, at least one outlet port is present on the second side 12 of the reactor. If desired, the inlet port 21 and such outlet port 12 may be reversed.

As shown in FIG. 2, the inlet ports 13-15 are suitably present in the upper cavity 4. This cavity 4 further leaves space for sensors 23. It will be understood by the skilled person that the bioreactor 1 is at its second side 12 preferably closed so as to maintain physical conditions in the best probable manner.

FIGS. 3 to 7 show a plurality of diagrammatical top views of the different embodiments of the carrier 7 in accordance with the inventions. All these embodiments show circular carriers 7 with open spaces 2 that are provided along several lines from the center 17 of the carrier 7 to its edge 18 so as to include rotational symmetry. It is however by no means excluded that the carriers 7 may have another shape. It is moreover not excluded that the open spaces 2 are oriented along circles at around the center 17 rather than on radial lines. The carrier comprises open spaces 2 and solid carriers 27.

Figure 3:
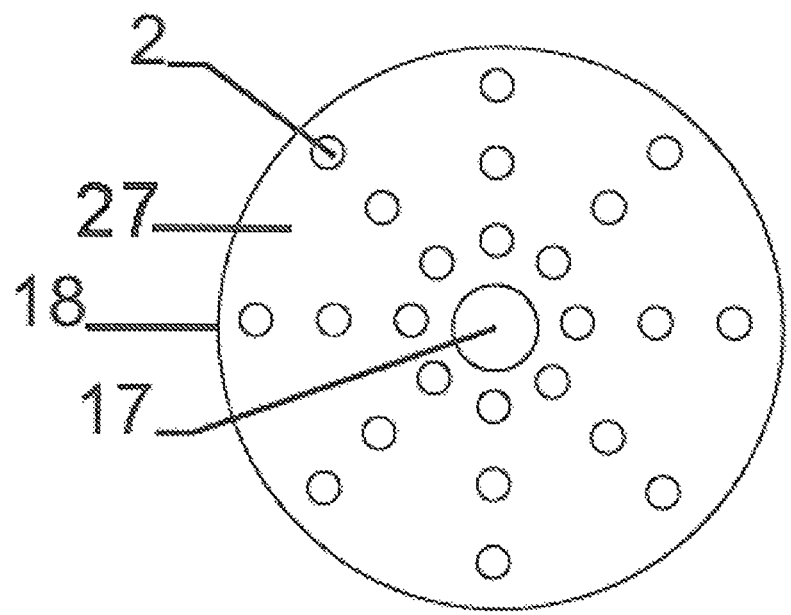
FIG. 3 shows a diagrammatical top view of a carrier according to a design for use in a bioreactor according to an embodiment of the disclosure.
Figure 4:
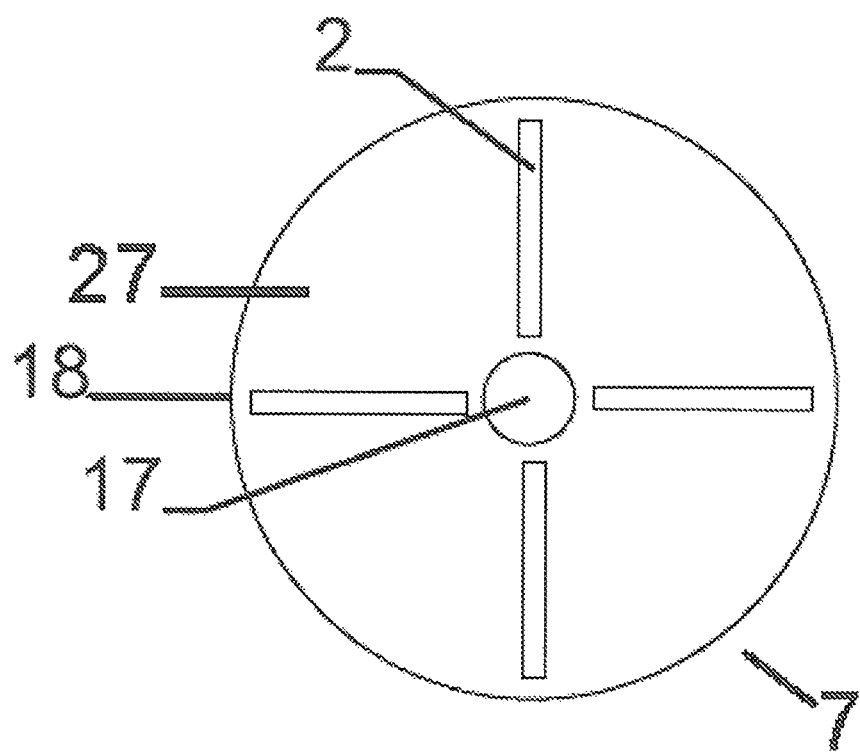
FIG. 4 shows a diagrammatical top view of a carrier according to a design for use in a bioreactor according to an embodiment of the disclosure.
Figure 5:
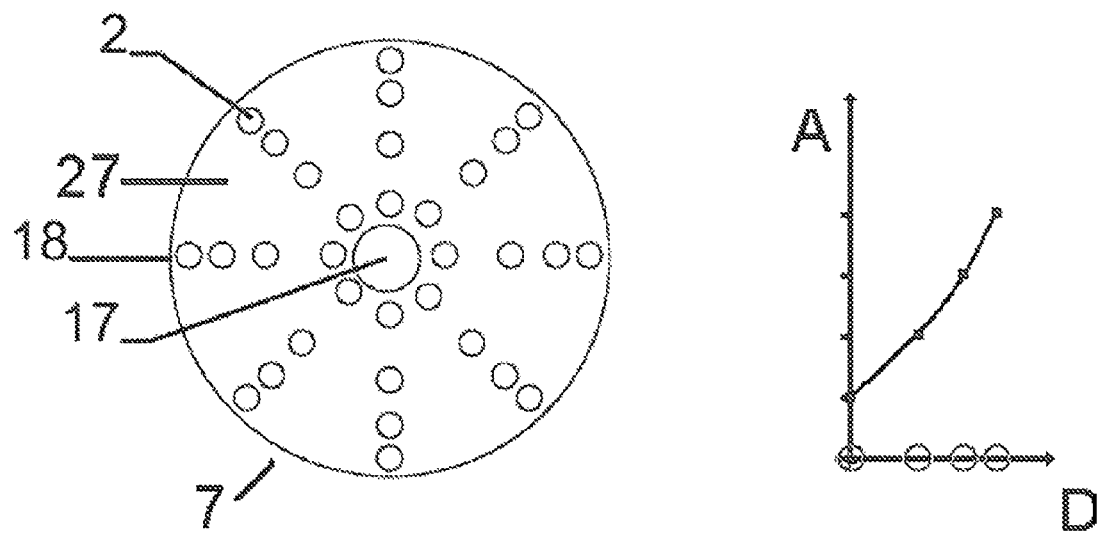
FIG. 5 shows a diagrammatical top view of a carrier according to a design for use in a bioreactor according to an embodiment of the disclosure (left); it also shows a graph showing that the overall surface area (A) covered by the open space in the carrier increases faster with increasing radial distance (D) to the geometrical center of the carrier.
Figure 6:
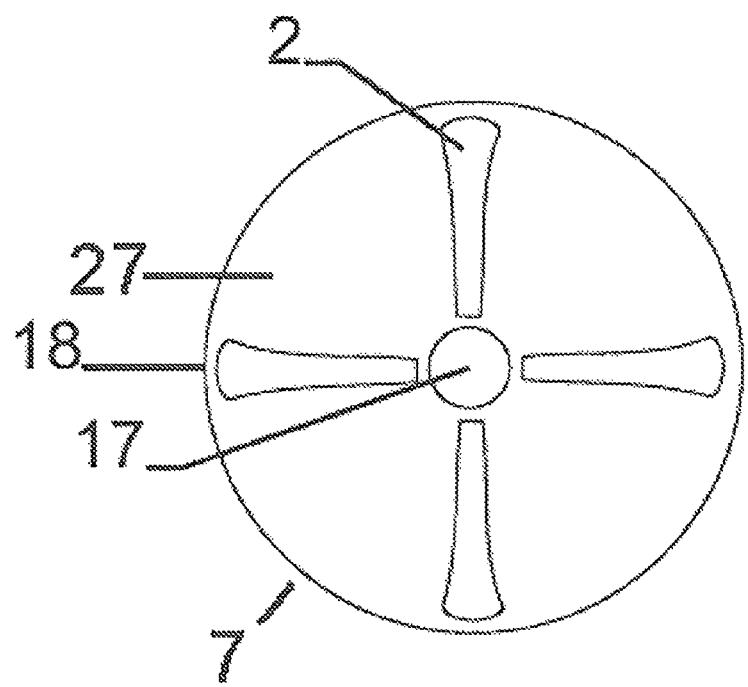
FIG. 6 shows a diagrammatical top view of a carrier according to a design for use in a bioreactor according to an embodiment of the disclosure.
Figure 7:
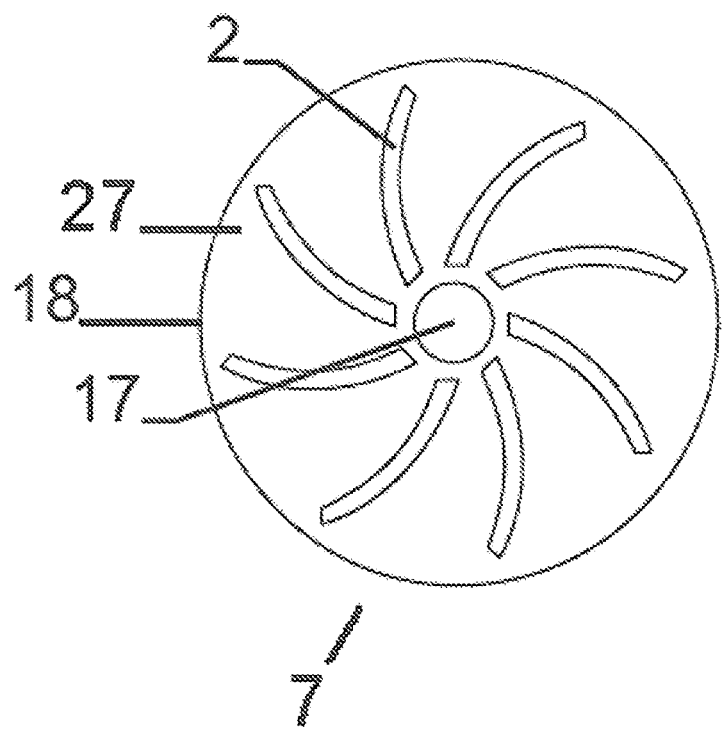
FIG. 7 shows a diagrammatical top view of a carrier according to a design for use in a bioreactor according to an embodiment of the disclosure.

FIGS. 3 and 5 show embodiments based on hole-shaped open spaces 2. FIGS. 4, 6 and 7 show embodiments based on groove-shaped open spaces 2, wherein grooves extend substantially from the center 17 to the side edge 18. Though not shown, the groove-shaped open spaces and the hole-shaped open spaces may be combined into a single carrier 7 design. Though not shown, the groove-shaped open spaces may be subdivided into a series of trench-shaped open spaces and the hole-shaped open spaces may be widened to get such trench-shaped open spaces.

FIGS. 3 and 4 show embodiments in which the surface area of the open space 2 is independent of the distance to the center 17. FIGS. 5 and 6 show embodiments in which the overall surface area covered by the open spaces 2 in at least one of the carrier 7 increases faster with increasing radial distance to the geometrical center of the carrier 7. FIG. 6 shows a preferred embodiment in which the surface area of the open spaces 2 increases with the distance to the center 17.

FIG. 5 shows thereof an implementation in which the density of open spaces 2, each of uniform size, increases with increasing radial distance to the center, e.g., by reduction of the spacing between individual open spaces 2.

FIG. 6 shows an implementation in which the width of the open spaces 2 increases with the distance to the center 17.

Figure 8:
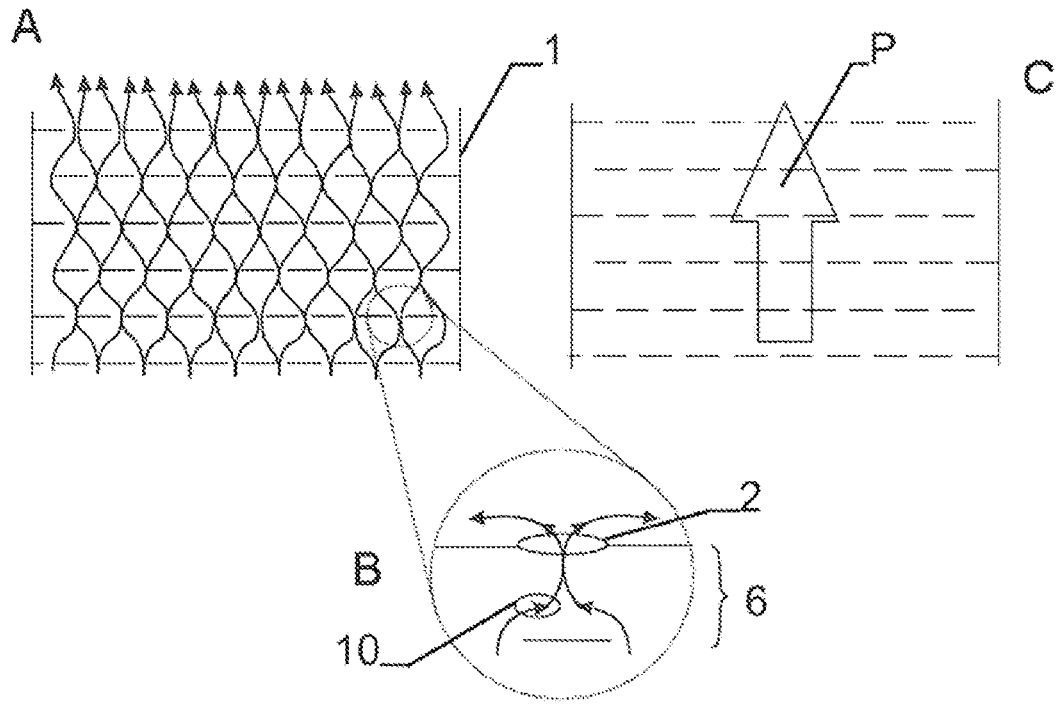
FIG. 8a-c shows figures for explanation of the flow in a bioreactor according to embodiments of the disclosure.

FIG. 7 shows a specific embodiment, in which the fluid interconnects 2 are defined so as to follow rotational movement of the medium in the bioreactor 1, which rotational movement is generated by a pumping system FIGS. 8a-c demonstrate the flow in the bioreactor in accordance with one embodiment of the invention. For ease of representation, an implementation is shown here, in which the open spaces 2 in a first carrier 7 are laterally, e.g., rotationally displaced with respect to the open spaces 2 in an adjacent second carrier 7. FIG. 8a herein discloses the flow on a microscale, while FIG. 8c discloses the flow on a macroscale. FIG. 8b illustrates the microscale in further detail. It will be clear that even though the flow on macroscale is along the principal direction P of the bioreactor 1, it includes on microscale a major component 10 extending laterally. FIG. 8b shows hereof a detailed view clarifying that effectively the flow is primarily lateral instead of primarily vertical. This is achieved through design, e.g., design of the width of the level 6, the size and density of the open spaces 2.

Figure 9:
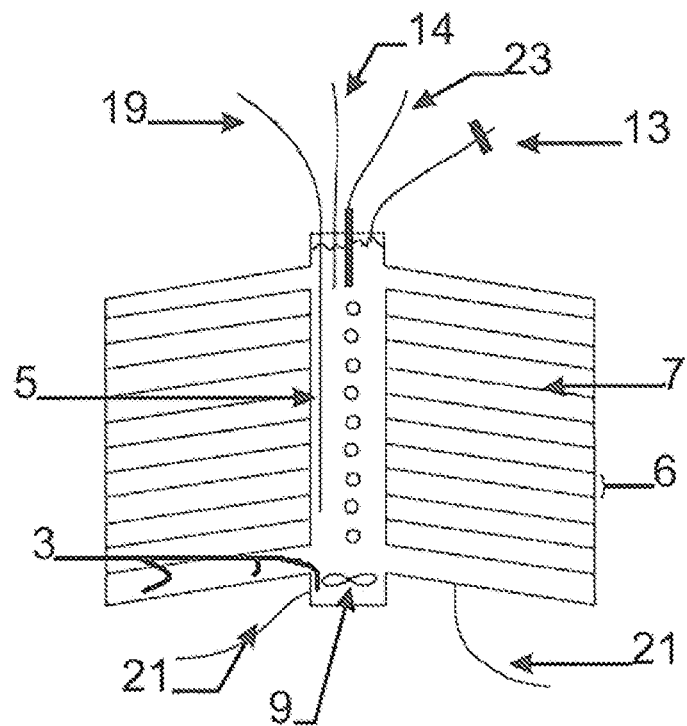
FIGS. 9 and 10 show diagrammatical cross-sectional views of further embodiments of the disclosure wherein the bioreactor comprises carriers including a non-perpendicular angle relative to the principal direction in the bioreactor.
Figure 10:
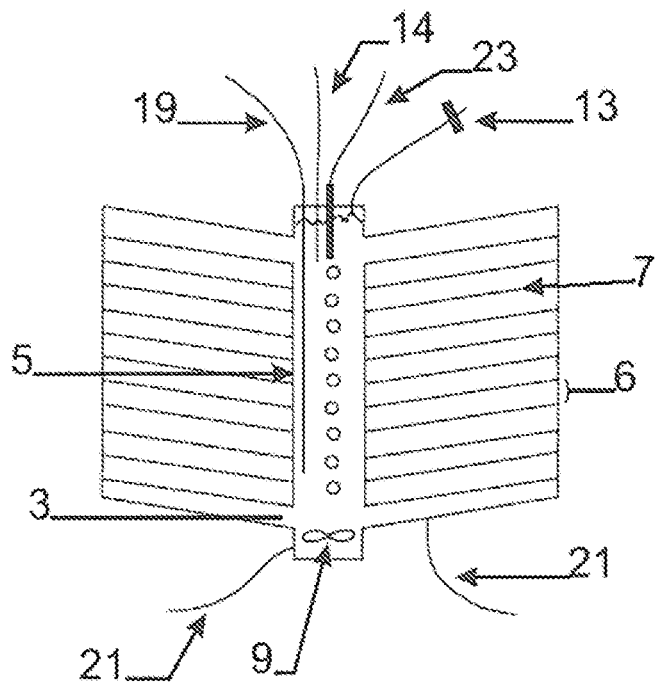
Figure 11:
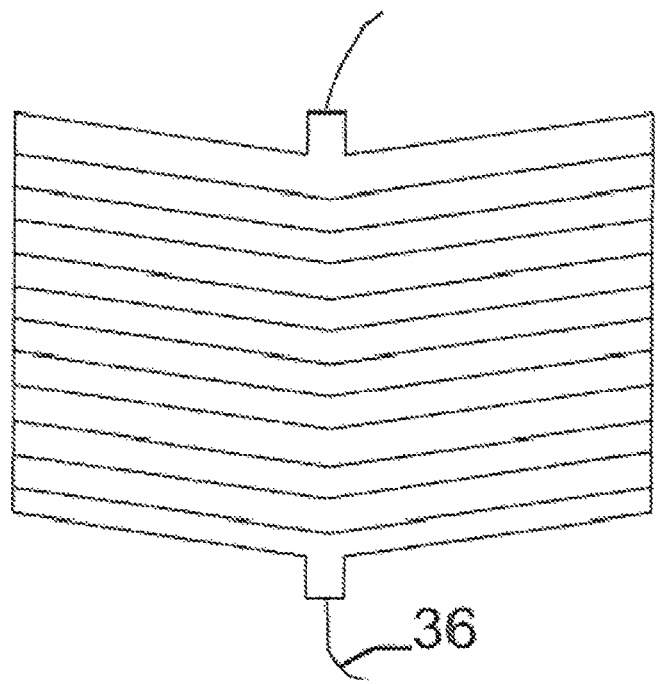
FIGS. 11 and 12 show diagrammatical cross-sectional views of further embodiments of the disclosure wherein the bioreactor comprises carriers including a non-perpendicular angle relative to the principal direction in the bioreactor.
Figure 12:
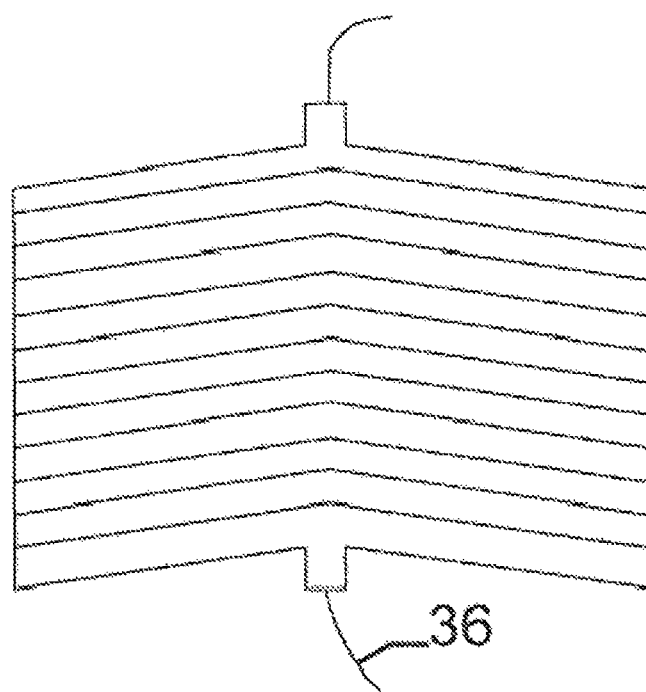
Figure 13:
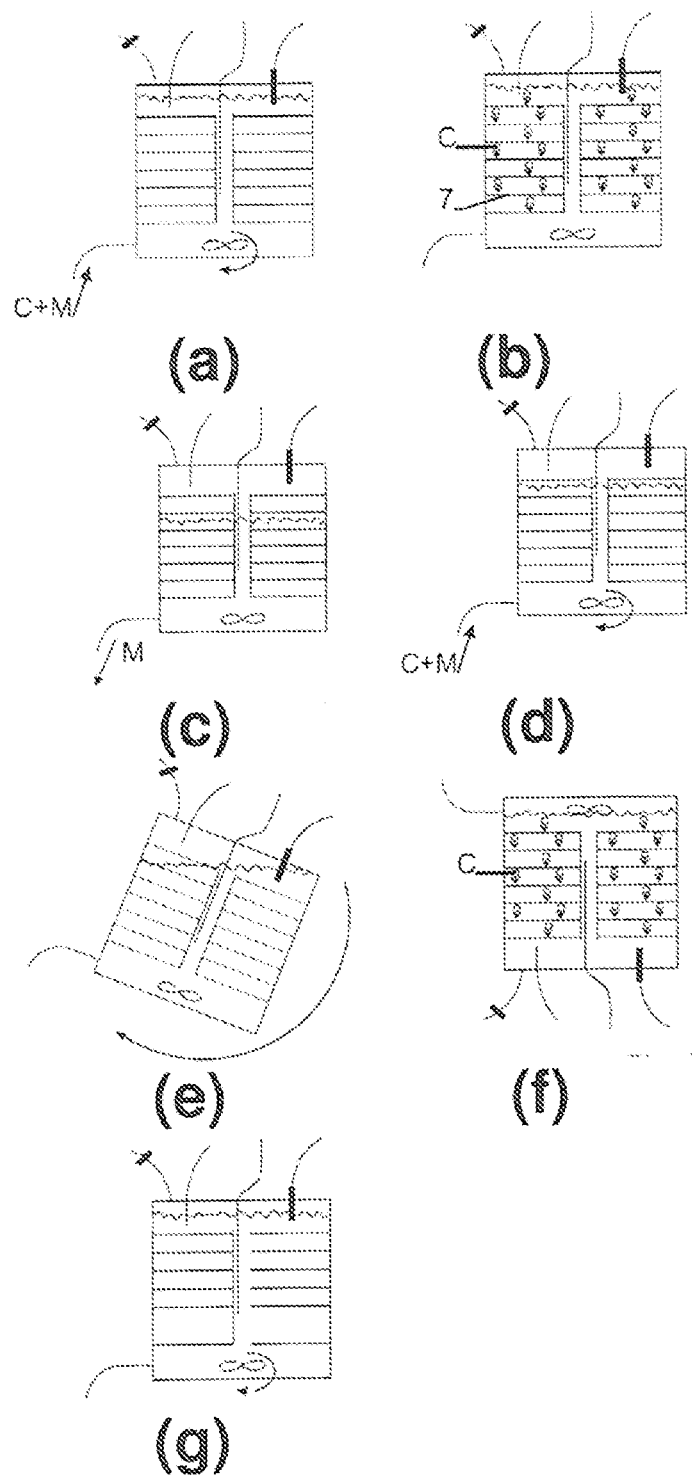
FIG. 13a-g shows a method according to an embodiment of the second aspect of the disclosure.

FIGS. 9 and 10 is a cross-sectional diagrammatical view of other embodiments of the bioreactor 1. The bioreactors 1 of these third and fourth embodiments are quite similar so that they will be discussed together. In these embodiments, the stack of carriers 7 is of conical shape, i.e., each of the carriers comprises at least a portion that includes a non-perpendicular (i.e., oblique) angle to the principal direction of the bioreactor. One advantage of such conical shape is that it simplifies bubble elimination between individual carriers. Furthermore, emptying and harvesting of the reactor is improved as the risk of forming puddles when emptying the reactor is avoided. While typically only one side of a carrier 7 is used for cell adhesion, it is not impossible that both sides of the carrier 7 are used for cell adhesion. One implementation thereof is the use of an impeller both in the upper cavity and the lower cavity (see FIG. 14). The orientation of the bioreactor may then be reversed. This allows that in a first operation cells are inserted and are allowed time to settle on a first carrier. Thereafter, the reactor orientation is reversed, and further cells are inserted (if needed) are allowed time to settle on the second carrier.

FIG. 13a-g shows a procedure for using both sides of each carrier in a bioreactor according to embodiments of the disclosure. In a first step (FIG. 13a), cells C in a medium M are introduced in the bioreactor 1 and the cells C are distributed homogeneously via operation of the impeller 9. In a second step (FIG. 13b), the cells C are allowed to settle on a first side of the carriers 7. The arrows stemming from the cells C show the direction of settlement. This is triggered by gravity. In a third step (FIG. 13c), the medium M is removed from the bioreactor 1. In a fourth step (FIG. 13d), further cells C in a medium M are introduced in the bioreactor 1 and the cells C are distributed homogeneously via operation of the impeller 9. In a fifth step (FIG. 13e), the bioreactor 1 is turned upside down after having switched off the impeller 9. In a sixth step (FIG. 13f), the cells C are allowed to settle on a second side of the carriers 7. In a seventh step (FIG. 13g), the bioreactor 1 is turned back in its initial orientation and the cells C can now grow on both sides of each carriers 7.

Figure 14:
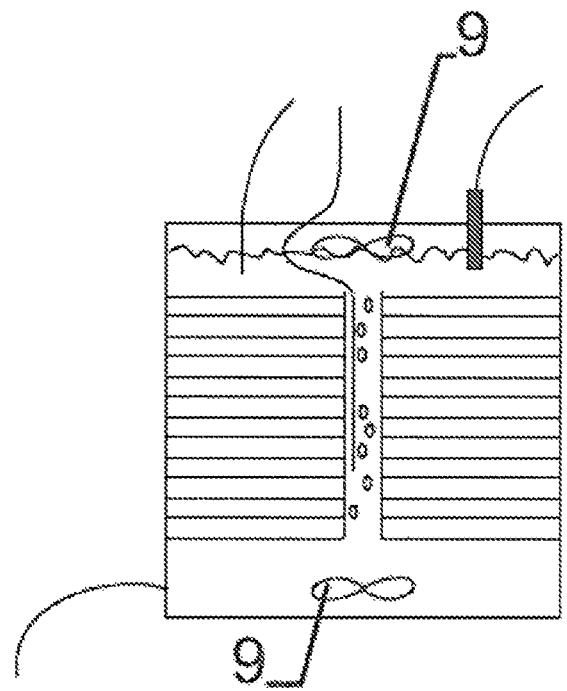
FIG. 14 shows a diagrammatical cross-sectional view of a bioreactor according to an embodiment of the disclosure.

FIG. 14 shows a bioreactor as in FIG. 2, wherein a second circulation means such as a pump is present in the upper cavity of the bioreactor. This reactor can operate upside down.

Figure 15:
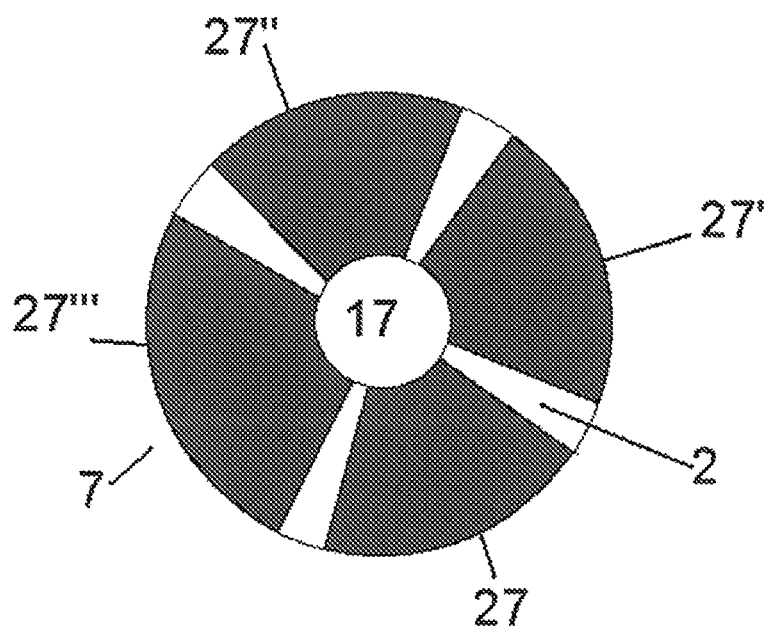
FIG. 15 shows a diagrammatical top view of a carrier according to a design for use in a bioreactor according to an embodiment of the disclosure.

FIG. 15 shows a carrier for use in a bioreactor according to embodiments of the disclosure in which the width of the open spaces 2 in the carrier 7 increases with the distance to the center 17. The carrier 7 is here composed of alternating solid carriers 27 and open spaces 2 separating laterally the solid carriers 27.

Figure 16:
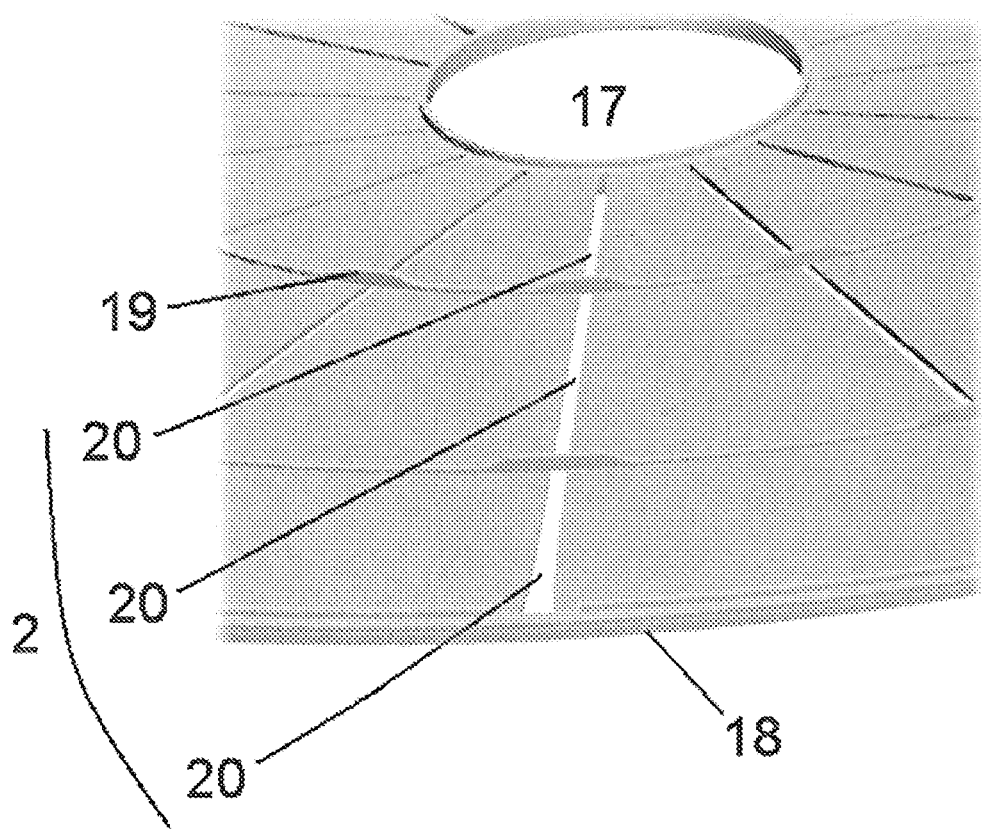
FIG. 16 shows a perspective view of a carrier according to a design for use in a bioreactor according to an embodiment of the disclosure.

FIG. 16 shows a portion of a carrier for use in a bioreactor according to embodiments of the disclosure in which open spaces 2 are bridged by ridges 19 thereby defining groove-shaped trenches 20.

Figure 17:
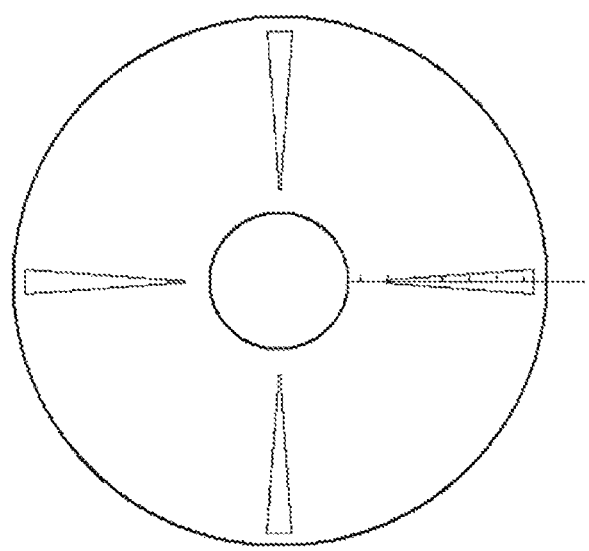
FIG. 17 shows a diagrammatical top view of a carrier according to a design for use in a bioreactor according to an embodiment of the disclosure (left); it also shows a graph showing that the overall surface area (A) covered by the open space in the carrier increases faster with increasing radial distance (D) to the geometrical center of the carrier.
Figure 17:
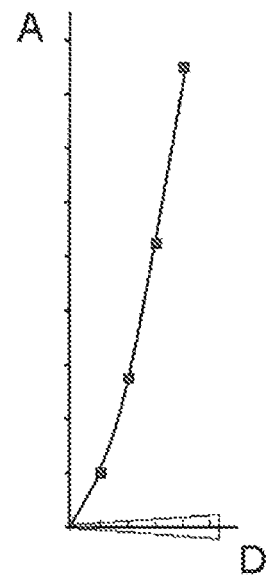

FIG. 17 shows a diagrammatical top view of a carrier according to a design for use in a bioreactor according to an embodiment of the disclosure (left); it also shows a graph showing that the overall surface area A covered by the open space in the carrier increases faster with increasing radial distance D to the geometrical center of the carrier (right).

Figure 18:
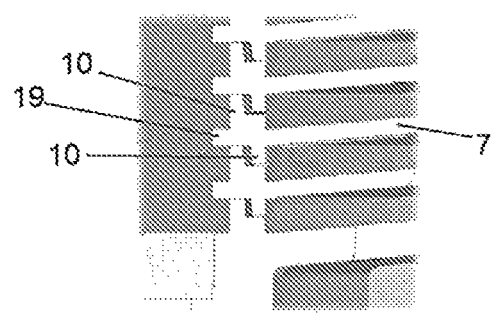
FIG. 18 shows a cross-sectional view of the edge of a stack of carriers for use in an embodiment of a reactor according to the disclosure.

FIG. 18 shows a cross-sectional view of the edge of a stack of carriers 7 for use in an embodiment of a reactor according to the disclosure. Visible are ridges 10 determining the inter-distance between two adjacent carriers 7 and the outward projecting ridges 19 that are meant to be embedded in a polymer material.

Figure 19:
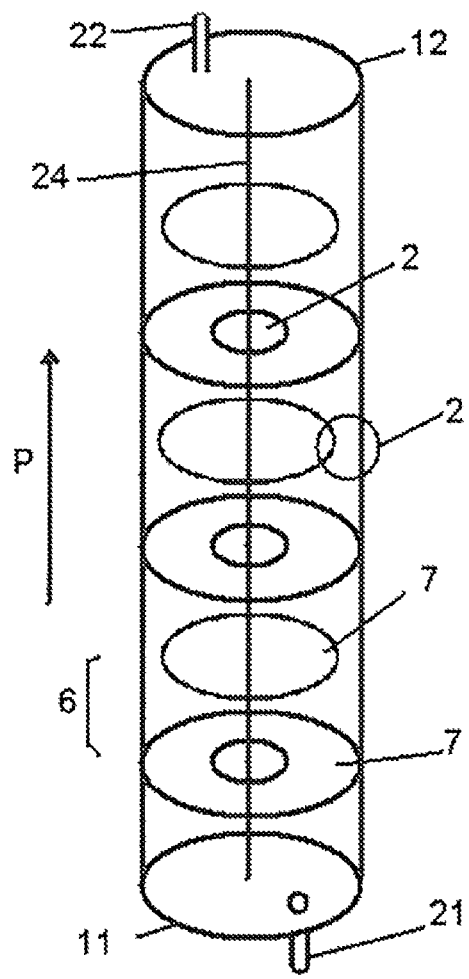
FIG. 19 shows a perspective view of a stack of carrier according to an embodiment of the disclosure.

FIG. 19 shows a perspective view of a bioreactor 1 for the culture of cells, comprising a stack of carrier 7 defining levels 6. The carriers 7 are of two alternative kinds. A first kind is hold in place by its edge and has a central open space. A second kind is hold in place by being attached to a central axis 24 and assures an open space for fluidly interconnecting two adjacent levels by not extending to the wall closing the stack.

Figure 20:
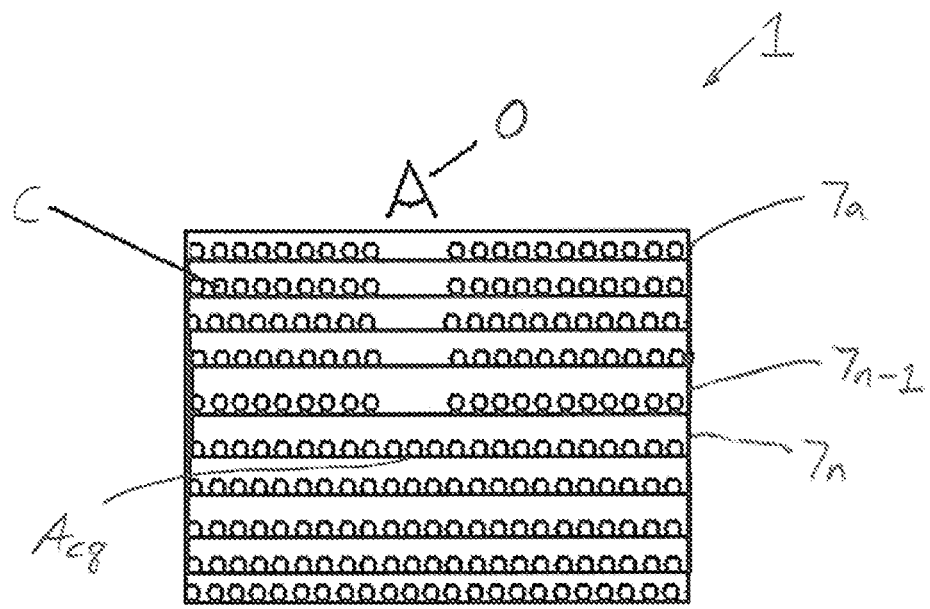
FIGS. 20-26 relate to a bioreactor according to an embodiment of the disclosure.

FIGS. 20-25 relate to an embodiment in which a cell culture device, such as bioreactor 1, includes carriers $7_a \ldots 7_n$, and is further adapted for viewing the growth of the cells C on one or more of the inner carriers from an exterior vantage point. In one possible approach, this may be achieved by providing an optically transparent line of sight from the external vantage point V to carrier $7_n$ through carriers $77_a \ldots 7_{n-1}$. In one particular embodiment, as shown in FIG. 20, this may be achieved by providing a surface area A on each carrier $7_a \ldots 7_{n-1}$ on which cells do not grow. This area may be achieved using a chemical treatment, such as by using a process to make the area hydrophobic to prevent cell adherence or growth, or instead by using a material that naturally retards or prevents cell adherence and adapting it for growth in areas besides area A (such as by using hydrophilization). These areas A among the carriers $7_a \ldots 7_{n-1}$ generally align, such that a substantially unobstructed line of sight is provided to a cell growth area $A_{cg}$ on carrier $7_n$. Thus, by using a microscope O or like device, the cells on this growth area $A_{cg}$ may easily be observed without interference from cell growth on carriers $7_a \ldots 7_{n-1}$. The area A may thus be considered as a window.

Figure 21:
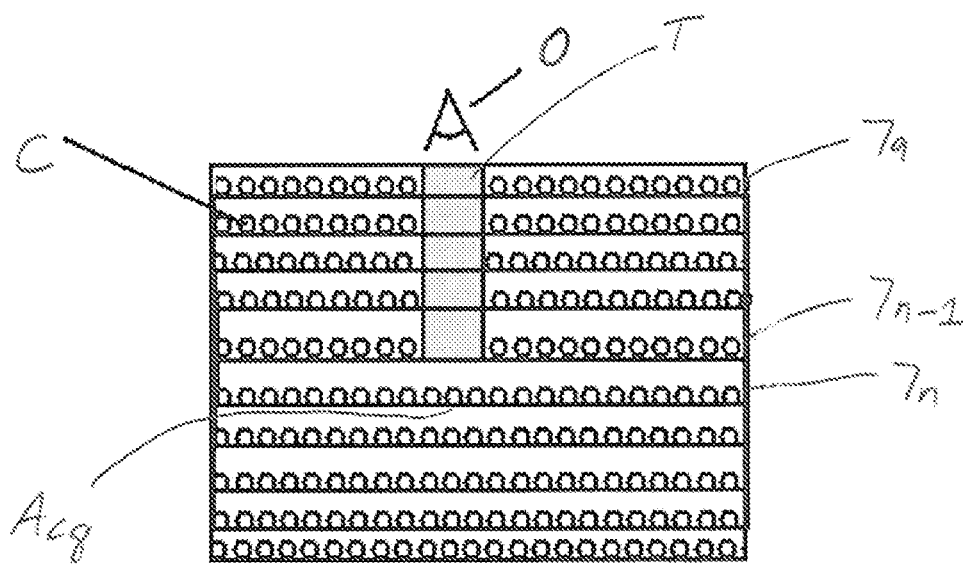

FIG. 21 shows an alternative embodiment, in which the desired line of sight is provided by providing an area A where cell growth is prevented by using an optically transparent material T associated with each carrier $7_a \ldots 7_{n-1}$, but not the carrier $7_n$ for which the cell growth observation is desired. Preferably, this material completely fills the space between adjacent carriers, and thus provides a substantially continuous optical path from the desired vantage point V. As with the previous embodiment, multiple lines of sight may be provided to provide observations at different levels of the bioreactor. In both embodiments, it is preferred that the area A is as small as possible to avoid minimizing the cell growth area while still permitting the desired observation to be made.

Figure 22:
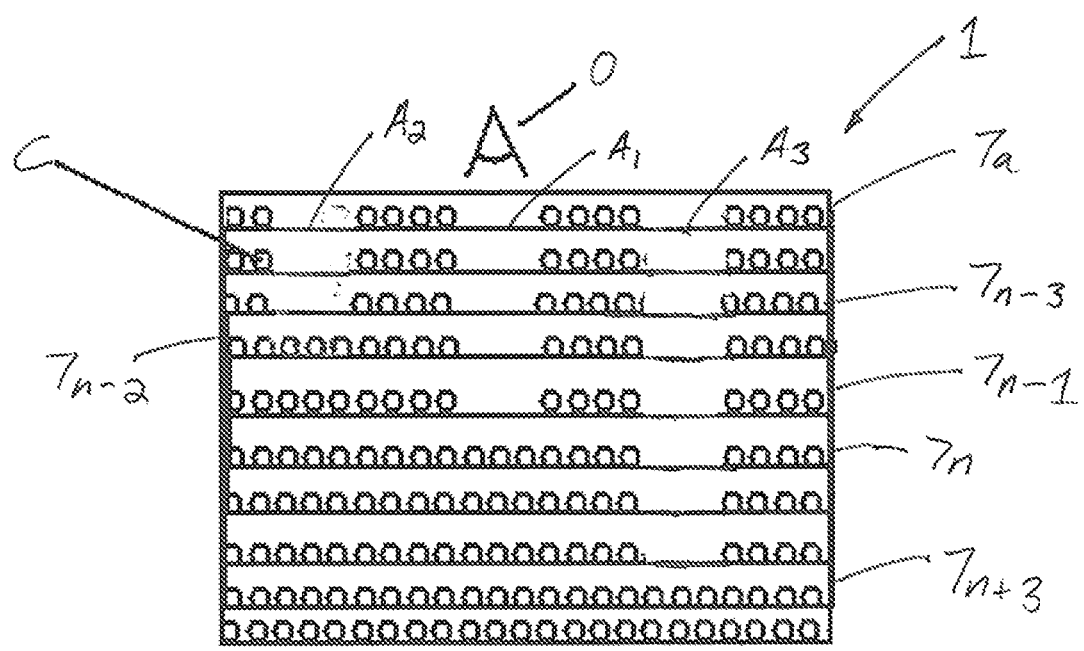

With reference to FIG. 22, it should be appreciated that different lines of sight may be provided for different carriers in the same device, such as bioreactor 1. Thus, for example, to view the cell growth on carrier $7_n$, the arrangement is as shown in FIG. 20, with areas $A_1$ on which cell growth is substantially prevented. For layer $7_{n-2}$, a different optical path is provided by similar areas $A_2$ on the corresponding carriers $7_a \ldots 7_{n-3}$. Furthermore, the path may be extended in a different area $A_3$ to reach the growth area of carrier $7_{n+3}$. As should be appreciated, this pattern may be repeated as necessary or desired to permit observation on one or more of the carriers.

Figure 23:
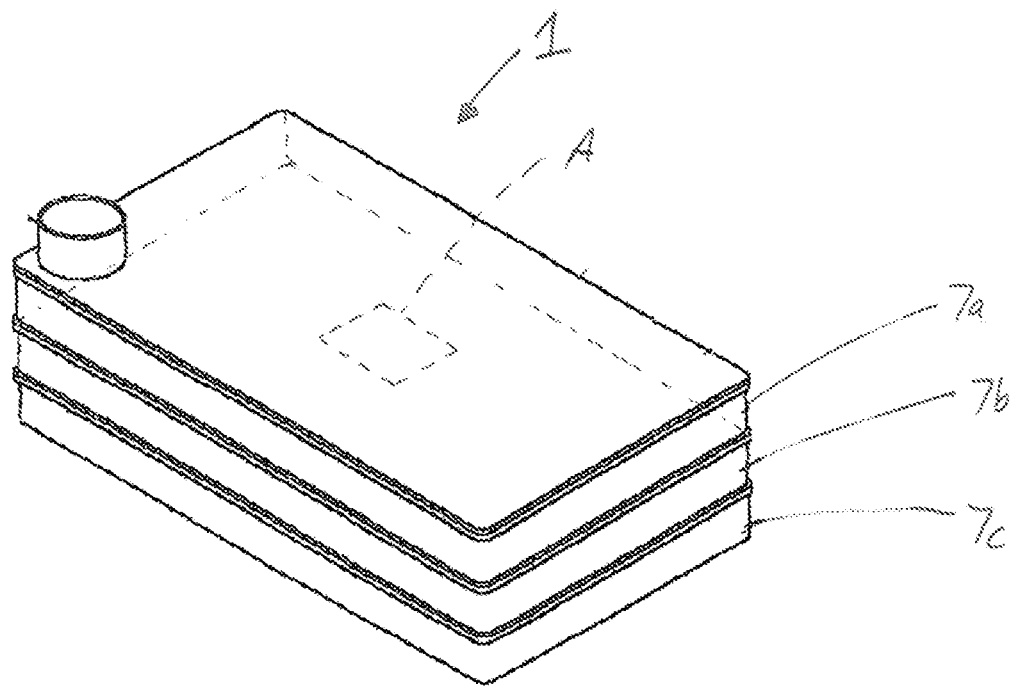
Figure 24:
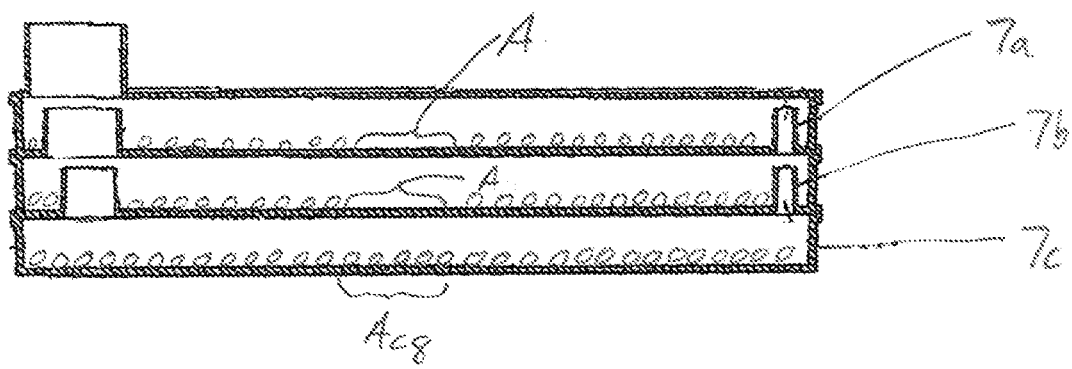
Figure 25:
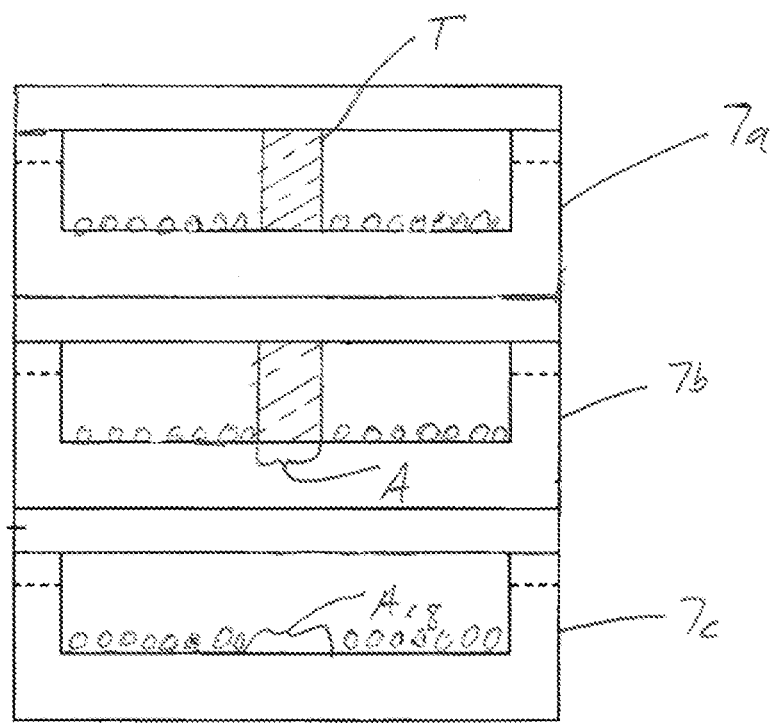

While it is possible to use these approaches to viewing the cell growth area in the cell culturing apparatus, such as bioreactor 1 with stacked carriers 7 within the same housing, as described herein, it also may find use in other applications. Thus, for example, FIGS. 23-25 illustrate the use of the embodiments described above in a cell culture device (which may comprise a bioreactor 1) comprising a plurality of stackable carriers $7_a$, $7_b$, and $7_c$, each having a separate inlet. In FIGS. 22-24, carriers $7_a$ and $7_b$ include areas A for preventing cell growth, which allows for the external observation through these areas to the growth area $A_{cg}$ on carrier $7_c$. Similarly, in FIG. 25, the optically transparent material T positioned in "cube" style carriers $7_a$ and $7_b$ form areas A for preventing cell growth, which allows for the external observation through these areas to the growth area $A_{cg}$ on carrier $7_c$ (which of course requires that any intervening portions of the carriers $7_a$ and $7_b$ are optically transparent to a sufficient degree to permit viewing in the desired manner). In either case, the ability to view lower layers avoids the costly and time-consuming need for having to unstack any upper carrier(s) in order to view the cell growth for the lower carrier(s).

Figure 26:
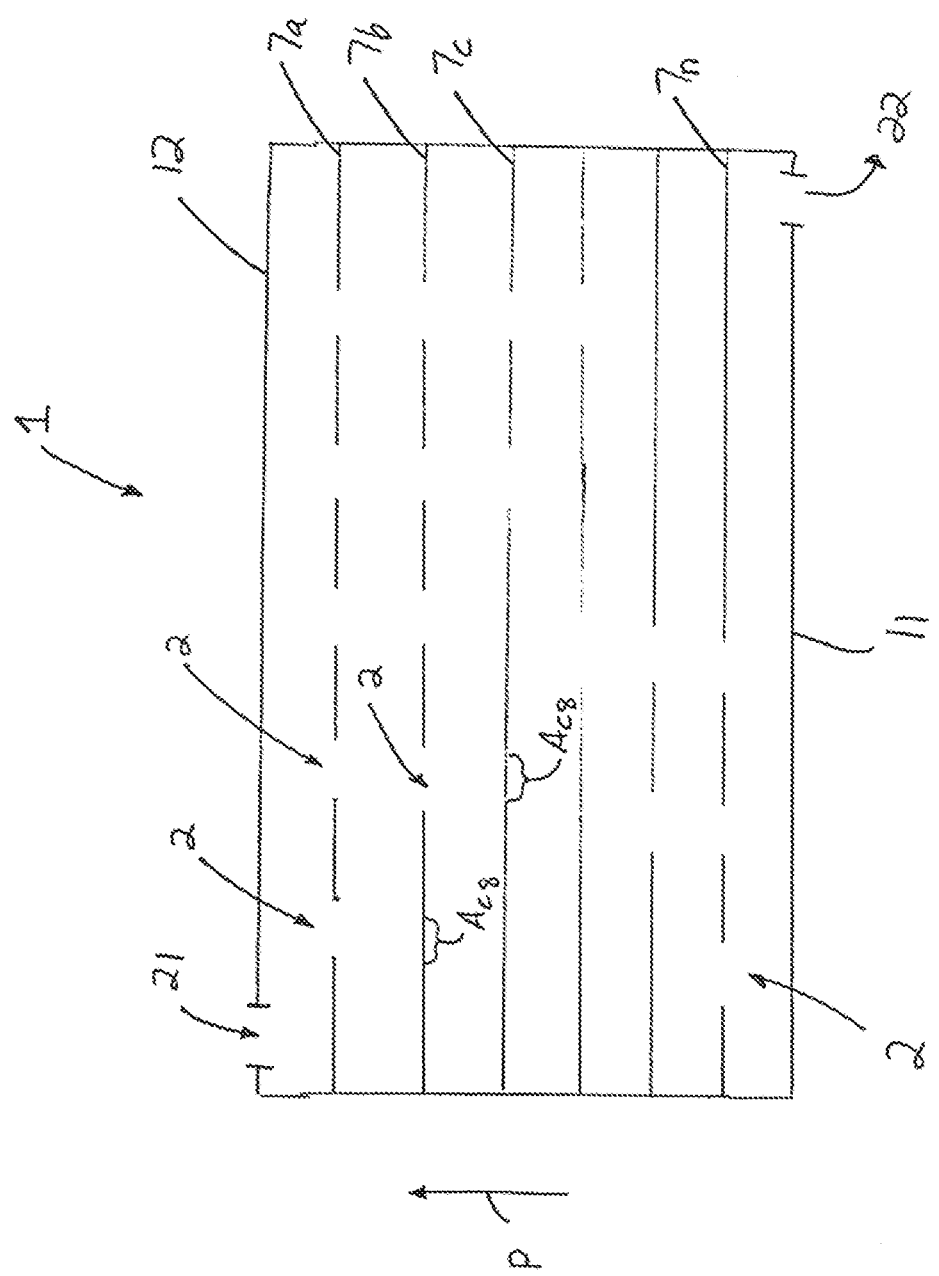

FIG. 26 shows an embodiment where the carriers $7_a \ldots 7_n$ include aligned openings to allow for the viewing of the cells on selected carriers. Specifically, the bioreactor 1 may include an inlet 21 and an outlet 22 positioned within a housing that contains a plurality of carriers arranged in a stacked configuration. A first carrier $7_a$ may be arranged so as to provide at least one open space 2 for allowing a direct view through the first side 12 of the housing (which is at least partially transparent for this purpose) to a growth area $A_{cg}$ on the next-adjacent carrier $7_b$. In like manner, the first and second carriers $7_a$ and $7_b$ may provide aligned open spaces 2 for providing a substantially continuous optical path to the next-adjacent carrier $7_c$. This pattern may be repeated as necessary or desired to allow for the viewing of the growth areas on selected carriers from an external vantage point, with the first carrier preferably having a number of openings corresponding to the innermost carrier to be viewed, and each successive carrier providing one fewer opening than the preceding one. Additionally, it is possible to combine or adapt this approach to allow for the viewing of carriers from the second side 11, as indicated by open space 2 in carrier $7_n$ (provided, of course, the housing is adapted for this purpose).

As should be appreciated, the open spaces 2 may also be arranged for ensuring the most desirable flow of fluid, oxygen, and nutrients to the layers, as outlined above. For instance, there may be two different sets of openings in the carriers (7), such as a first set devoted to "zig-zag" flow for cell nutrition, and a second set of aligned openings for observation (and, most preferably, arranged such that the "straight" flow through the aligned openings create is low relative to the main flow through the offset openings).

As used herein and unless provided otherwise, the term "comprising" is not synonym of the term "consisting" which has a narrower meaning. The term "comprising" should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the disclosure, the only relevant components of the device are A and B. Moreover, the term "comprising" always includes the term "consisting" and when the term "comprising" appears in an embodiment of the disclosure, this same embodiment wherein the term "consisting" replaces the term "comprising" is always also an embodiment of the disclosure.

Furthermore, the terms "first", "second", "third" and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms "top", "bottom", "over", "under" and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

Reference throughout this specification to "one embodiment" or "an embodiment" means that a particular feature, structure or characteristic described in connection with the embodiment is included in at least one embodiment of the disclosure. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

As used herein and unless provided otherwise, the term "length" relates to the longest dimension of an object (e.g., an open space).

As used herein and unless provided otherwise, the term "width" relates to the largest dimension of an object taken at right angle to its length. The "width" is therefore never longer than the "length".

The foregoing descriptions of various embodiments of the invention are provided for purposes of illustration, and are not intended to be exhaustive or limiting. Modifications or variations are also possible in light of the above teachings. The embodiments described above were chosen to provide the best application to thereby enable one of ordinary skill in the art to utilize the disclosed inventions in various embodiments and with various modifications as are suited to the particular use contemplated. All such modifications and variations are within the scope of the invention.

The invention claimed is:

1. A bioreactor (1) for the culture of cells (C), comprising a stack of carriers (7) for cell (C) adherence and liquid medium (M) distribution, the carriers (7) forming levels (6) between adjacent carriers (7) for the flow of the liquid medium (M) and at least one fluid channel (5) separate from the stack of carriers (7) providing a fluid connection between a first carrier (7) at a first end of the stack of carriers (7) and a second carrier (7) at a second end of the stack of carriers (7), therewith providing a circulation system for the liquid medium (M), wherein adjacent levels (6) are fluidly interconnected to each other via a plurality of open spaces (2) in each of the carriers so that the liquid medium (M) can flow from one level (6) to an adjacent level (6) through the open spaces, wherein a first open space (2) between a first and an adjacent second level (6') does not overlap with a second open space (2) between the second level (6') and an adjacent third level (6").

2. The bioreactor (1) according to claim 1, wherein the open spaces do not overlap in a vertical direction (P).

3. The bioreactor (1) according to claim 1, wherein at least one of the carriers (7) is provided by a single plate or membrane wherein the open spaces (2) are apertures in the single plate or membrane.

4. The bioreactor (1) according to claim 3, wherein each of the carriers (7) is provided by a single plate and/or membrane comprising the apertures.

5. The bioreactor according to claim 1, wherein the open spaces (2) comprise grooves in the carriers.

6. The bioreactor (1) according to claim 1, wherein the open spaces (2) in the carriers (7) are symmetrical.

7. The bioreactor (1) according to claim 1, wherein the overall surface area covered by the open spaces (2) in at least one of the carriers (7) increases with increasing radial distance from the geometrical center of the carrier (7).

8. The bioreactor (1) according to claim 1, wherein at least one of the open spaces (2) gets wider with increasing radial distance from the geometrical center of the carrier (7).

9. The bioreactor (1) according to claim 1, wherein the ratio between the overall surface area covered by the open spaces (2) and the overall surface area covered by a solid portion of at least one carrier (7) is from 1% to 10% of the area of the carrier.

10. The bioreactor (1) according to claim 1, wherein at least one of the carriers (7) has at least a portion that is oriented in a direction including a non-perpendicular angle to the principal direction (P), which portion comprises at least one open space (2).

11. The bioreactor (1) according to claim 1, wherein at least one of the carriers (7) is oriented having a major surface with a non-perpendicular angle to a principal direction (P) of flow of the liquid medium in the bioreactor (1).

12. The bioreactor (1) according to claim 1, wherein the carriers (7) are conical.

13. The bioreactor (1) according to claim 1, wherein the carriers (7) include at least one side edge (18) provided with at least one side ridge (10), side ridges (10) of a first and a second adjacent carrier (7) defining a mutual distance between the carriers (7) at the side edge (18).

14. The bioreactor (1) according to claim 1 wherein the levels (6) defined between adjacent carriers (7) are hermetically closed at the side edges (18) of the carriers (7).

15. The bioreactor (1) according to claim 1, further comprising at least one circulation means (9) for driving the flow of the liquid medium (M) within the bioreactor (1).

16. The bioreactor according to claim 1, wherein the fluid channel (5) is concentric to the stack of carriers (7) and internal or external to the stack of carriers (7).

17. The bioreactor (1) according to claim 16, wherein the fluid channel (5) is a central column internal to the stack of carriers (7).

18. The bioreactor (1) according to claim 1, further comprising an upper cavity and a lower cavity adjacent to respectively the first and the second extremity of the stack of carriers (7) and in fluid communication therewith and with the fluid channel (5).

19. The bioreactor (1) according to claim 18, further comprising inlet/outlet ports to the upper (4) and/or lower cavity (3).

20. The bioreactor (1) according to claim 18, wherein an at least one inlet port (21) is present in the lower cavity (3) and at least one outlet port (22) is present in the upper cavity (4) and external circulation means are coupled between the inlet (21) and outlet ports (22).

21. The bioreactor according to claim 1, further comprising a probe (23) for measuring a parameter of the liquid medium (M).

22. The bioreactor according to claim 21, further comprising a controller connected to the probe (23) for modifying the parameter in function of the input received by the controller from the probe (23).

23. The bioreactor according to claim 1, wherein alternating carriers in the stack have alternatively a central open space and a peripheral open space.

24. The bioreactor (1) according to claim 1, wherein the open spaces (2) have a ratio length to width from 1 to 4.

25. The bioreactor (1) according to claim 1, wherein the open spaces (2) are circular.

26. The bioreactor (1) according to claim 1, wherein the number of the open spaces (2) per unit area of the carriers is constant on the whole surface of the carriers.

27. The bioreactor (1) according to claim 17, further including a tube within the central column for providing one or more components into the medium within the central column.

28. A bioreactor (1) for the culture of cells (C), comprising a stack of carriers (7) for cell (C) adherence, the carriers (7) including a first carrier at a first extremity of the stack to a second carrier (7) at a second extremity of the stack so as to define levels (6) between adjacent carriers (7) for the flow of the liquid medium (M), wherein adjacent levels (6) are fluidly interconnected so that the liquid medium (M) can flow from one level (6) to an adjacent level (6), wherein the bioreactor further comprises at least one fluid channel separate from the stack and concentric with the stack, providing a mechanical connection between the first carrier (7) and the second carrier (7), therewith providing a circulation system for the liquid medium (M) wherein the fluid channel (5) is internal to the stack of carriers (7) and wherein the fluid channel does not have fluid connections to individual levels extending between adjacent carriers.

29. The bioreactor (1) according to claim 28, further including a hollow tube forming the fluid channel, said hollow tube providing a fluid connection between a first carrier at a first extremity of the stack of carriers and a second carrier at a second extremity of the stack of carriers.

* * * * *